(12) United States Patent
Packard et al.

(10) Patent No.: US 10,307,123 B2
(45) Date of Patent: Jun. 4, 2019

(54) TOMOSYNTHESIS VIEWS FROM CONE BEAM COMPUTED TOMOGRAPHY DATA

(71) Applicant: Carestream Health, Inc., Rochester, NY (US)

(72) Inventors: Nathan J. Packard, Rochester, NY (US); John Yorkston, Penfield, NY (US); Richard A. Simon, Rochester, NY (US); Levon O. Vogelsang, Webster, NY (US); Robert A. Senn, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 175 days.

(21) Appl. No.: 15/350,470

(22) Filed: Nov. 14, 2016

(65) Prior Publication Data

US 2017/0143288 A1    May 25, 2017

Related U.S. Application Data

(60) Provisional application No. 62/259,703, filed on Nov. 25, 2015.

(51) Int. Cl.
*A61B 6/00* (2006.01)
*A61B 6/03* (2006.01)
*A61B 6/02* (2006.01)
*A61B 6/04* (2006.01)

(52) U.S. Cl.
CPC ............. *A61B 6/463* (2013.01); *A61B 6/025* (2013.01); *A61B 6/032* (2013.01); *A61B 6/035* (2013.01); *A61B 6/04* (2013.01); *A61B 6/4085* (2013.01); *A61B 6/4441* (2013.01); *A61B 6/465* (2013.01); *A61B 6/466* (2013.01); *A61B 6/467* (2013.01); *A61B 6/505* (2013.01); *A61B 6/5205* (2013.01); *A61B 6/5223* (2013.01)

(58) Field of Classification Search
CPC ....... A61B 6/025; A61B 6/032; A61B 6/4085; A61B 6/5205
See application file for complete search history.

(56) References Cited

U.S. PATENT DOCUMENTS

| | | | |
|---|---|---|---|
| 8,233,690 B2 | 7/2012 | Ng et al. | |
| 8,280,135 B2 | 10/2012 | McCollough et al. | |
| 2015/0104089 A1* | 4/2015 | Litvin | G06T 11/006 382/131 |

OTHER PUBLICATIONS

Commonly assigned: U.S. Pat. No. 8,818,065, granted Aug 26, 2014, titled: Methods and Apparatus for Scatter Correction for CBCT System and Cone-Beam Image Reconstruction, assigned to Carestream Health, Inc.

* cited by examiner

*Primary Examiner* — Dani Fox

(57) ABSTRACT

An imaging method, accesses cone beam computed tomography (CBCT) data and displays, on a display monitor, at least one view of the CBCT data. The method provides an interface for a user to indicate a tomosynthesis reconstruction plane on the displayed view of the CBCT data; and displays a tomosynthesis image on the display monitor according to the indicated tomosynthesis reconstruction plane.

20 Claims, 41 Drawing Sheets

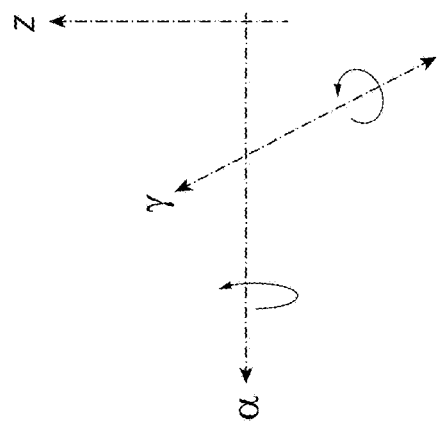
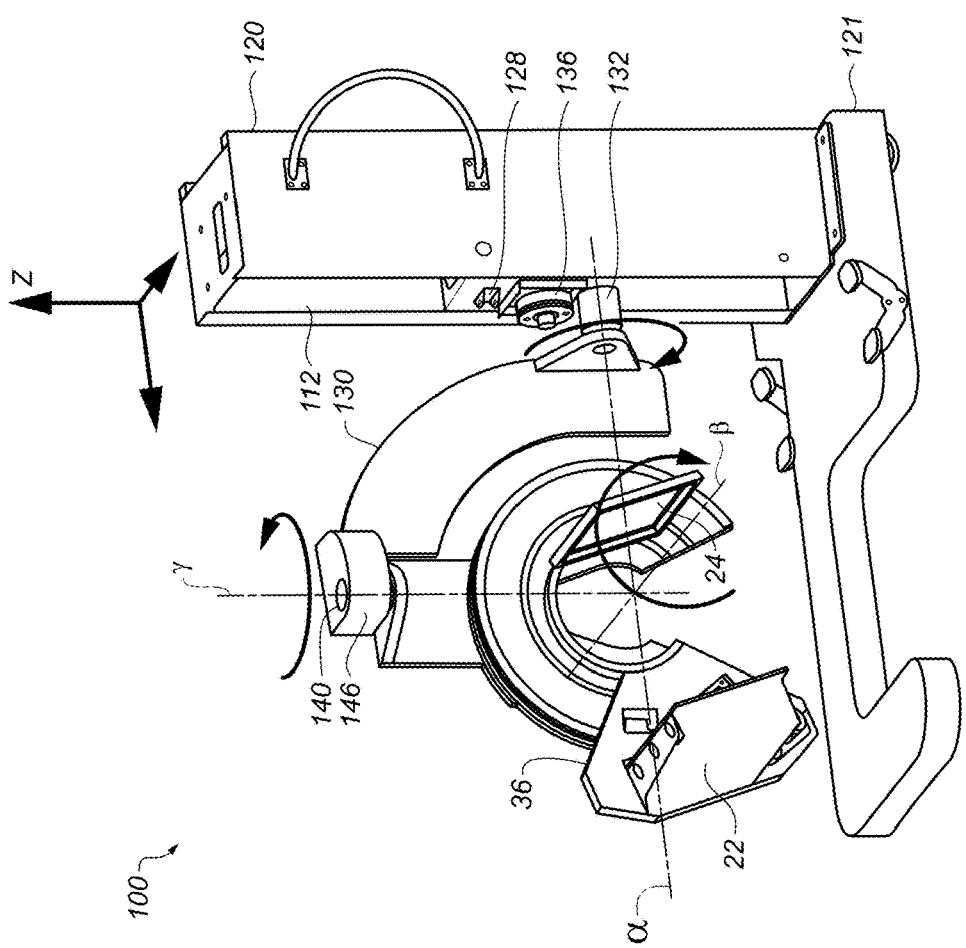

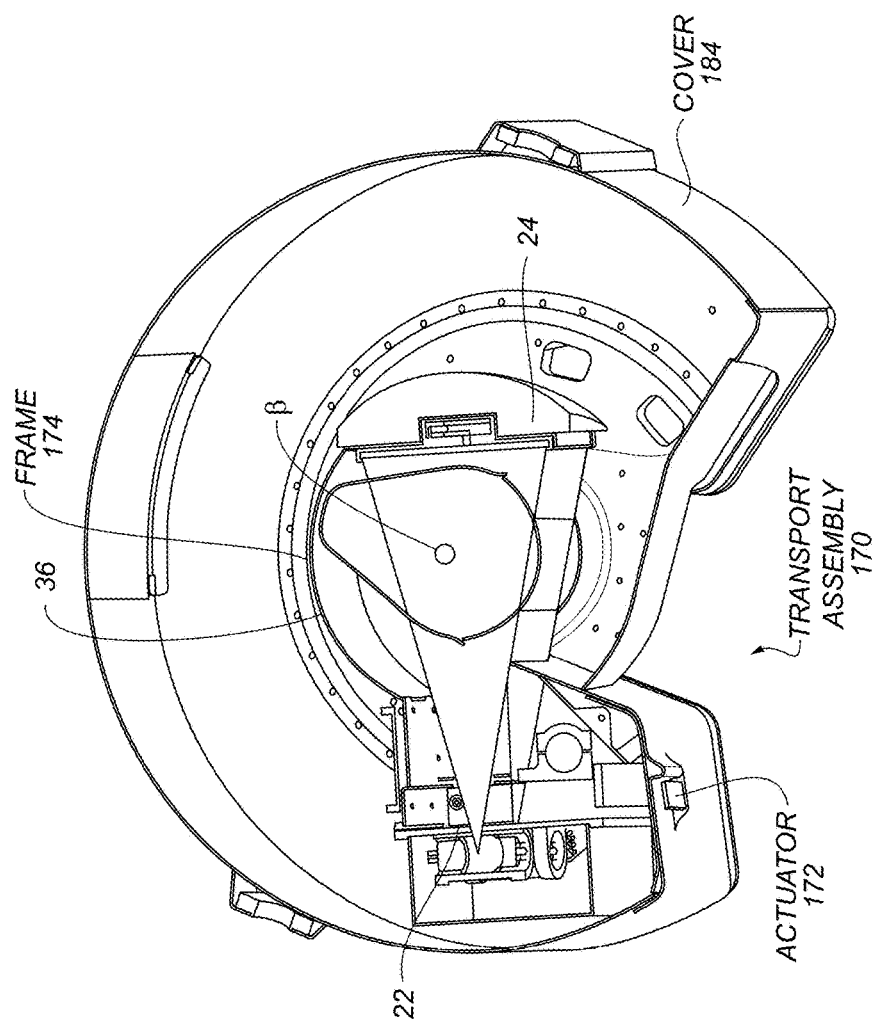

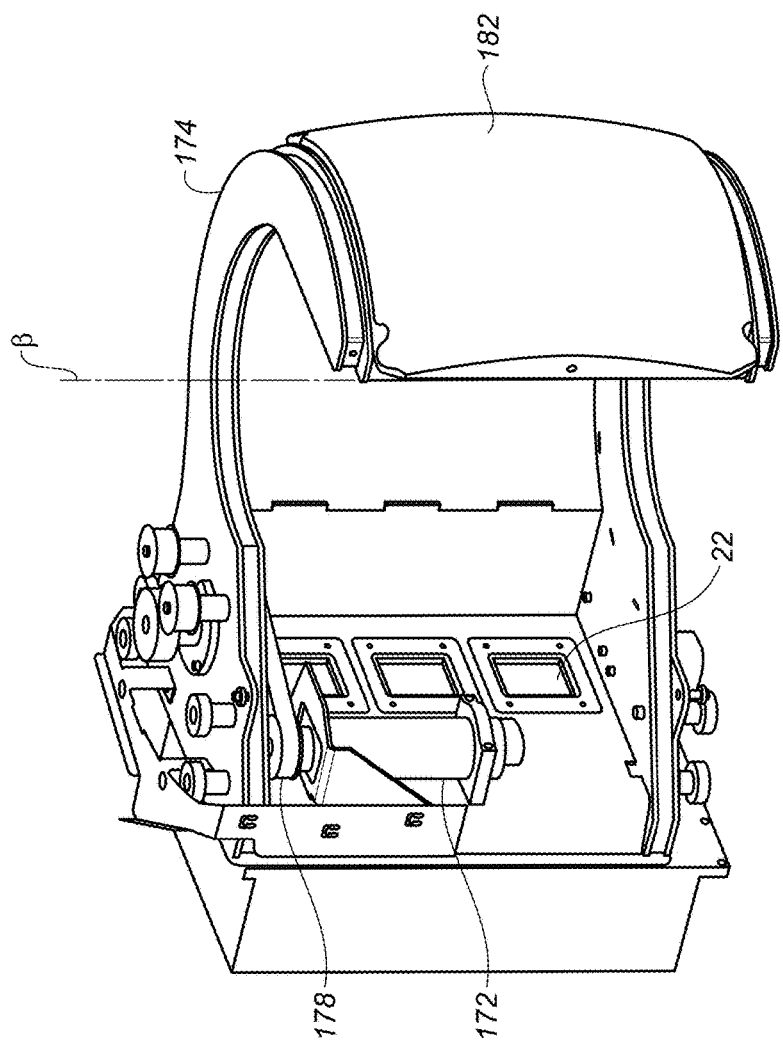

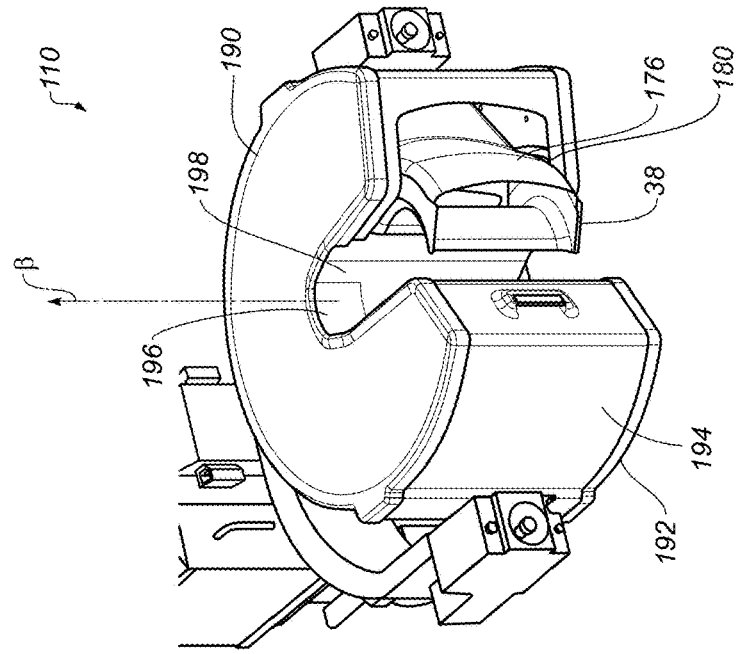
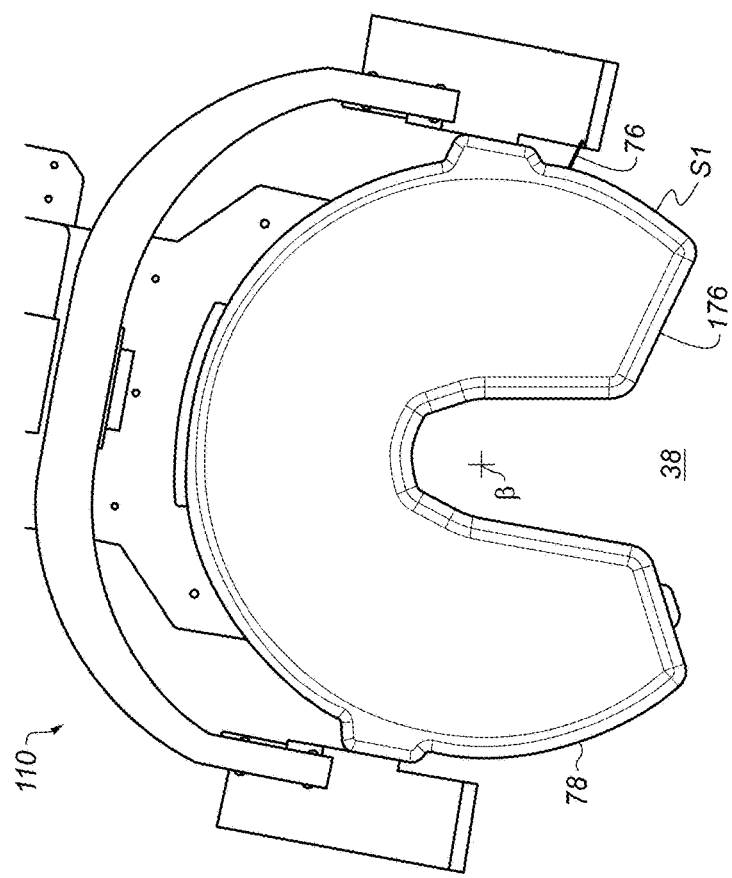
FIG. 16B
FIG. 16A

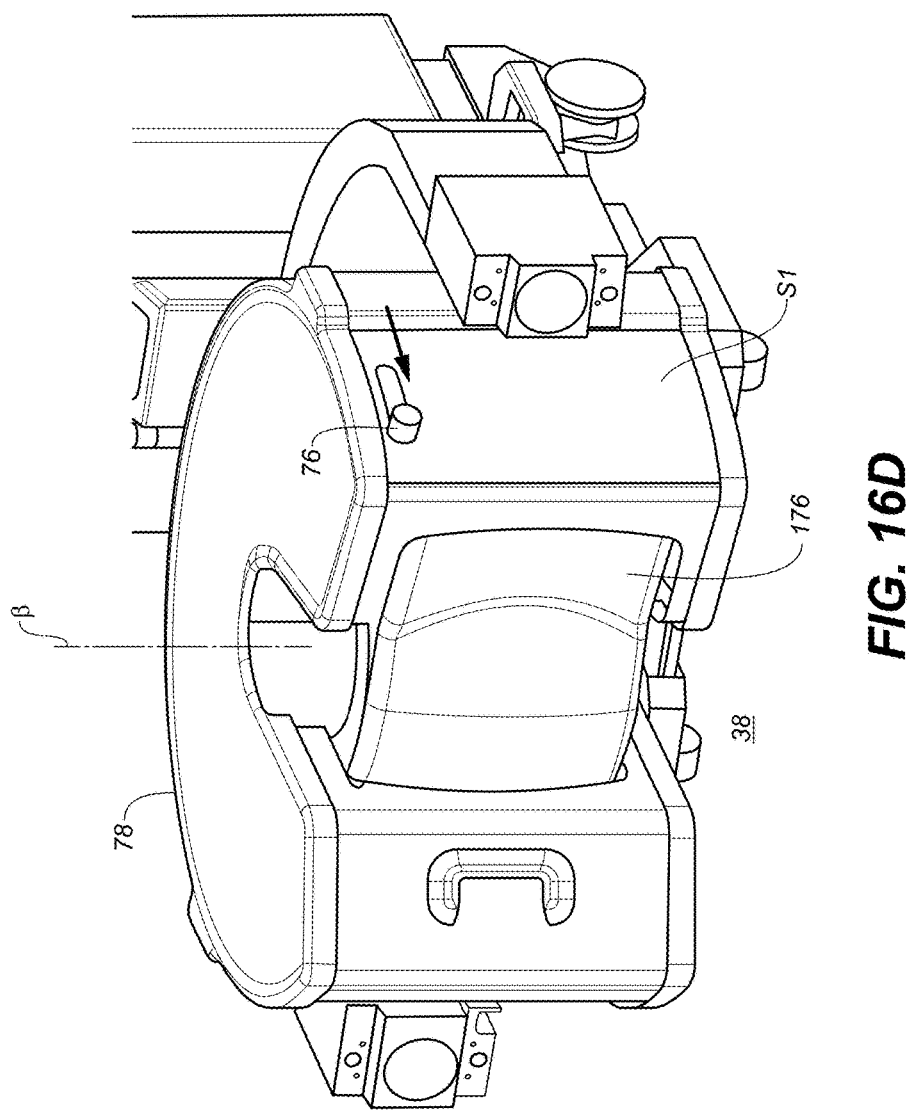

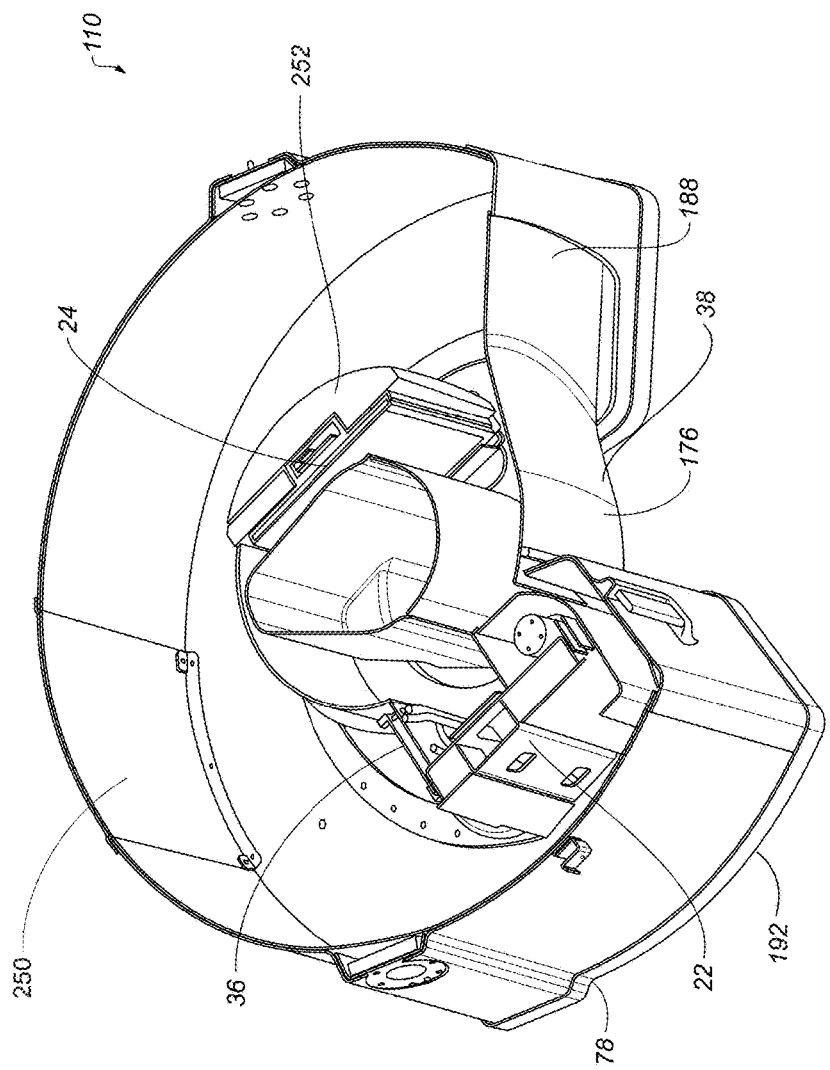

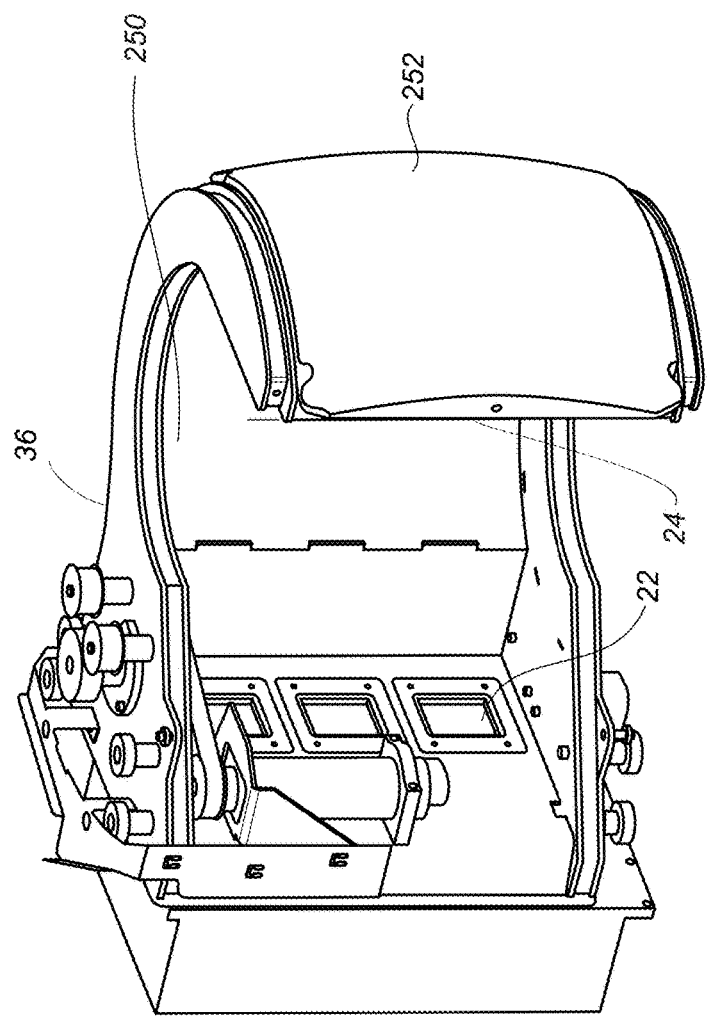

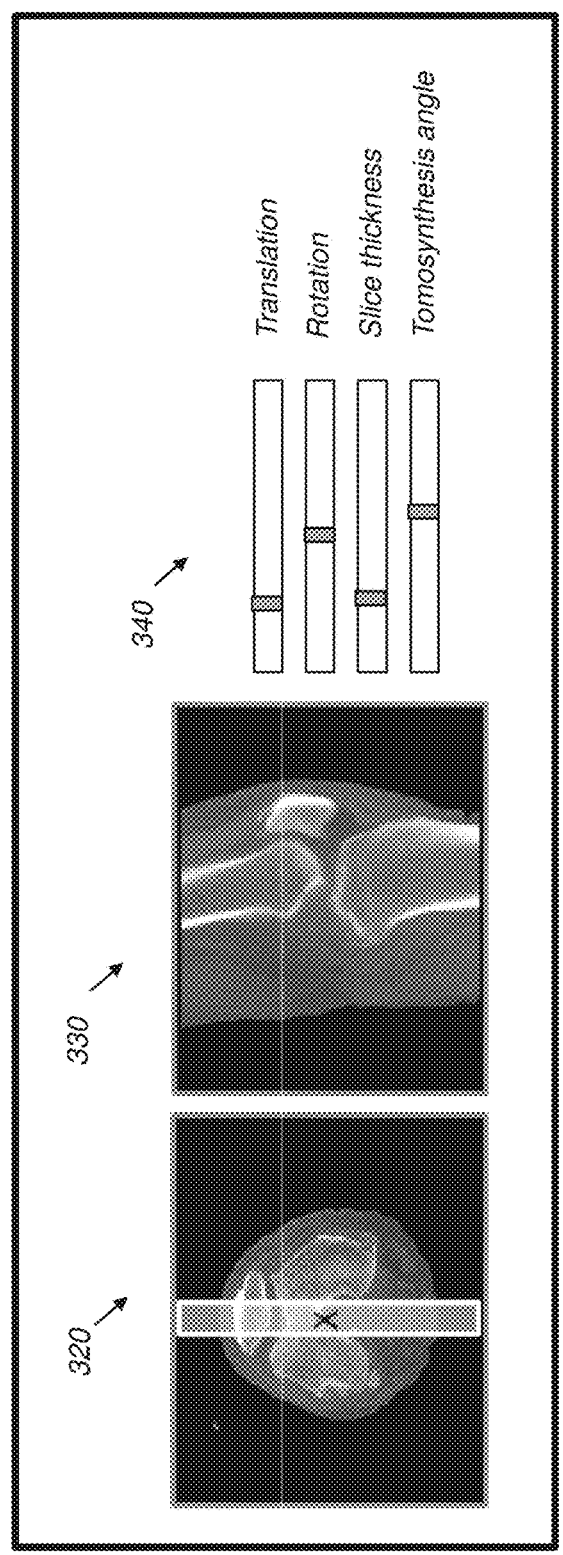

TOMOSYNTHESIS VIEWS FROM CONE BEAM COMPUTED TOMOGRAPHY DATA

CROSS REFERENCE TO RELATED APPLICATIONS

This application claims the benefit of U.S. Provisional Ser. No. 62/259,703, filed on Nov. 25, 2015, entitled "TOMOSYNTHESIS VIEWS FROM CONE BEAM COMPUTED TOMOGRAPHY DATA", in the names of Nathan J. PACKARD, John YORKSTON, Richard A. SIMON, Levon O. VOGELSANG, and Robert A. SENN, incorporated herein in its entirety.

FIELD OF THE INVENTION

The invention relates generally to the field of medical imaging and more particularly to display of volume images.

BACKGROUND

Tomosynthesis, cone beam computed tomography (CBCT) or cone beam CT, and computed tomography (CT) are well known medical imaging methods, helpful for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Apparatus for tomosynthesis and CBCT are known. Such apparatus include a support structure; a scanner assembly coupled to the support structure, and includes a digital detector to capture an image by the detector; a radiation source; and a control system coupled to the support structure to provide an interface for operation of the apparatus. The detector moves along a detector path, wherein the detector path has a distance that is sufficiently long to allow a scan volume to be positioned within the detector path.

Cone beam computed tomography (CBCT) or cone beam CT technology provides a diagnostic tool for providing 3-D volume images. Cone beam CT systems capture volumetric data sets by using a DR detector and an x-ray source. The source and detector are typically affixed to a gantry that rotates about the object to be imaged. The source directs, from various points along its orbit around the subject, a divergent cone beam of x-rays toward the subject. The CBCT system captures projections throughout the rotation, for example, one 2-D projection image at every degree of rotation. The projections are then used in reconstruction of a 3D volume image using various reconstruction techniques. Among well known methods for reconstructing the 3-D volume image from the 2-D image data are filtered back projection (FBP) approaches. CBCT systems can be particularly useful for imaging legs, arms, and other extremities.

Tomosynthesis, also referred to as digital tomosynthesis, is a method for performing high-resolution limited-angle tomography at radiographic dose levels. Tomosynthesis has been adapted for a variety of clinical applications, including vascular imaging, dental imaging, orthopedic imaging, mammographic imaging, musculoskeletal imaging, and chest imaging. Tomosynthesis combines digital image capture and processing with simple tube/detector motion as used in conventional computed tomography (CT).

However, though similar to CT in some aspects, tomosynthesis has some differences that characterize it as a separate technique. In CT, for example, the source/detector arrangement typically makes at least a complete 180-degree plus fan angle revolution about the subject obtaining a complete set of data from which fully 3-D volume images may be reconstructed. Digital tomosynthesis, on the other hand, uses a limited range of rotation angles (e.g., 15-60 degrees) with a lower number of discrete exposures (e.g., 7-51) than CT, which can obtain hundreds of 2-D projection images. This incomplete set of projections for tomosynthesis is digitally processed to yield images with some of the depth representation of conventional tomography, but having a sharply limited depth of field. Because the image processing is digital, a series of slices at different depths and with different thicknesses can be reconstructed from the same acquisition. However, since fewer tomosynthesis projections are needed than CT to perform the reconstruction, radiation exposure and cost are significantly reduced.

Reconstruction algorithms for tomosynthesis are similar to those used for conventional CT. To handle the computational complexity of these algorithms, a number of manufacturers have produced practical systems using off-the-shelf graphical processing units (GPUs) that can perform full 3-D volume reconstruction in a few seconds.

U.S. Pat. No. 8,233,690 (Ng), incorporated herein in its entirety by reference, describes a dynamic tomographic image reconstruction and rendering on-demand.

U.S. Pat. No. 8,280,135 (McCollough), incorporated herein in its entirety by reference, is directed to a system and method for highly attenuating material artifact reduction in x-ray computed tomography.

Medical practitioners use tomosynthesis in a number of diagnostic applications, such as for a range of extremity imaging functions, where the full 3-D volume of CT is not necessary and where the added complexity of handling metal-related artifacts and other volume imaging artifacts present cost and computational burden that can make accurate diagnosis more difficult. There is a need to provide tomosynthesis representation of volume data even where the full set of CT image data might otherwise be available.

SUMMARY OF THE INVENTION

An aspect of this application is to advance the art of medical digital radiography, particularly for providing tomosynthesis for extremities and other anatomy. An aspect of this application is to address, in whole or in part, at least the foregoing and other deficiencies in the related art and to provide, in whole or in part, at least the advantages described herein.

It is another aspect of this application to advance the art of diagnostic imaging of extremity body parts, particularly jointed or load-bearing, paired extremities such as knees, legs, ankles, fingers, hands, wrists, elbows, arms, and shoulders.

According to an embodiment of the present disclosure, there is provided an imaging method, comprising: accessing cone beam computed tomography (CBCT) data; displaying, on a display monitor, at least one view of the CBCT data; providing an interface for a user to indicate a tomosynthesis reconstruction plane on the displayed at least one view of the CBCT data; and displaying a tomosynthesis image on the display monitor according to the indicated tomosynthesis reconstruction plane.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 6A shows internal components used for imaging ring translation and positioning.

FIG. 6B shows reference axes for rotation and translation.

FIG. 15A is a top view of the scanner components of an extremity imaging apparatus according to an embodiment of the application.

FIG. 15C is a perspective view of a frame that supports scanner components of an extremity imaging apparatus with added counterweight according to an embodiment of the application.

FIG. 16A is a top view of the imaging scanner showing the door open position.

FIG. 16B is a perspective view of the imaging scanner showing a door closing position.

FIG. 16D is a perspective view showing the door in closed position.

FIG. 20 shows shielding provided for internal components of the scanner housing.

FIG. 21 shows shielding provided along the gantry, including a backing plate behind the detector.

FIGS. 26A and 26B show first and second rows, respectively, of images shown in FIG. 25.

DETAILED DESCRIPTION

Figure 2:
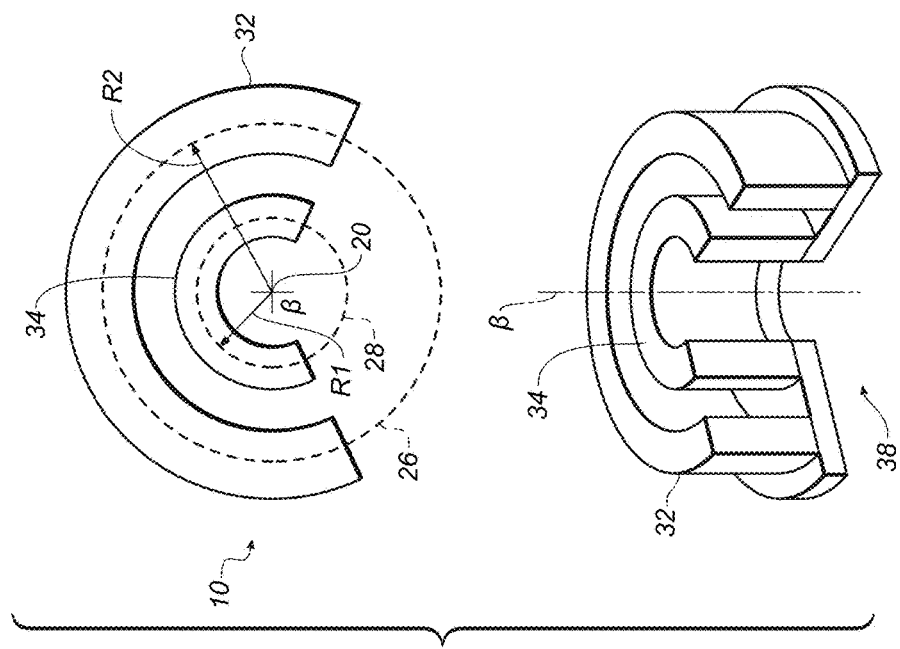
FIG. 2 shows a top and perspective view of the scanning pattern for an imaging apparatus according to an embodiment of the application.

The following is a description of exemplary embodiments of the invention, examples of which are illustrated in the accompanying drawings. Wherever possible, the same reference numbers will be used throughout the drawings to refer to the same or like parts.

For illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention.

In the context of the application, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity of the patient that is imaged, such as the "subject leg", for example. The term "paired extremity" is used in general to refer to any anatomical extremity wherein normally two or more are present on the same patient. In the context of the application, the paired extremity is not imaged unless necessary; only the subject extremity is imaged. In one embodiment, a paired extremity is not imaged to reduce patient dose.

A number of the examples given herein for extemporary embodiments of the application focus on imaging of the load-bearing lower extremities of the human anatomy, such as the leg, the knee, the ankle, and the foot, for example. However, these examples are considered to be illustrative and non-limiting.

In the context of the present disclosure, the terms "viewer", "operator", or "user" are used equivalently and denote the radiologist, physician, or other health professional who uses the apparatus and methods of the present disclosure to manipulate and view volume images.

In the context of the application, the term "arc" or, alternately, or arcuate has a meaning of a portion of a curve, spline or non-linear path, for example as being a portion of a curve of less than 360 degrees or, considered alternately, of less than 2π radians for a given radius or distance from a central bore.

The term "actuable" has its conventional meaning, relating to a device or component that is capable of effecting an action in response to a stimulus, such as in response to an electrical signal, for example.

As used herein, the term "energizable" relates to a device or set of components that perform an indicated function upon receiving power and, optionally, upon receiving an enabling signal.

In the context of the application, two elements are considered to be substantially orthogonal if their angular orientations differ from each other by 90 degrees, +/− no more than about 10 degrees.

It is instructive to observe that the mathematical definition of a cylinder includes not only the familiar "can-shaped" right circular cylinder, but also any number of other shapes. The outer surface of a cylinder is generated by moving a first straight line element along a closed curve or other path along a base plane, while maintaining the first straight line element parallel to a second, fixed straight line that extends out from the base plane, wherein the moving first straight line intersects a fixed closed curve or base in the base plane. A cube, for example, is considered to have a cylindrical shape according to this definition. A can-shaped cylinder of revolution, for example, is generated when the moving first straight line intersects a circle in the base plane at a right angle. An object is considered to be substantially cylindrical when its overall surface shape is approximated by a cylinder shape according to this definition, with allowance for standard edge rounding, protruding or recessed mechanical and electrical fasteners, and external mounting features.

Certain exemplary embodiments according to the application address the difficulties of extremity imaging by providing an imaging apparatus that defines coordinated non-linear source and detector paths (e.g., orbital, curved, concentric about a center point), wherein components that provide the source and detector paths are configured to allow patient access prior to and following imaging and configured to allow the patient to sit or stand with normal posture during the CBCT image capture series. Certain exemplary embodiments provide this capability by using a detector transport device that has a circumferential access opening allowing positioning of the extremity, wherein the detector transport device is revolved about the positioned extremity once it is in place, enclosing (e.g., partially, substantially, fully) the extremity as it revolves through at least a portion of the scan.

It is instructive to consider dimensional attributes of the human frame that can be considerations for design of CBCT equipment for scanning extremities. For example, an adult human patient of average height in a comfortable standing position has left and right knees generally anywhere from about 10 to about 35 cm apart. For an adult of average height, exceeding about 35-40 cm (14-15.7 inches) between the knees becomes increasing less comfortable and out of the range of normal standing posture. It is instructive to note that this constraint makes it impractical to use conventional gantry solutions for obtaining the needed 2-D image sequence. For certain exemplary embodiments, either the source or the detector must be able to pass between the legs of a standing patient for knee CBCT imaging, a capability not available with gantry or other conventional solutions.

Although 3-D images of diagnostic quality can be generated using CBCT systems and technology, a number of technical challenges remain. In some cases, for example, there can be a limited range of angular rotation of the x-ray source and detector with respect to the subject. CBCT Imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy often prevents the radiation source and image detector from being positioned over a portion of the scan circumference.

Figure 1:
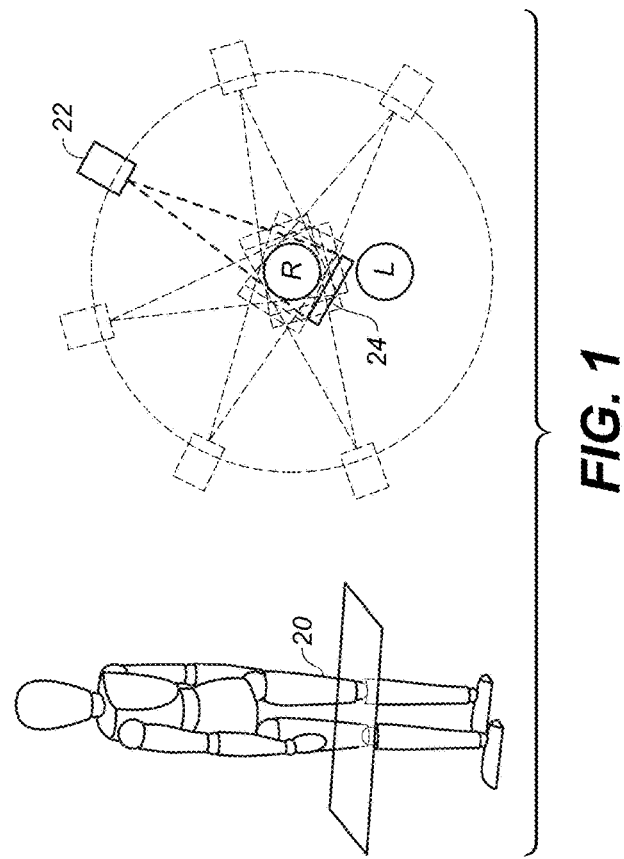
FIG. 1 is a schematic view showing the geometry and limitations of CBCT scanning for portions of the lower leg.

To illustrate issues associated with the CBCT imaging of the knee, the top view of FIG. 1 shows the circular scan paths for a radiation source 22 and detector 24 when imaging the right knee R of a patient as a subject 20. Various positions of radiation source 22 and detector 24 are shown in dashed line form. Source 22, placed at some distance from the knee, can be positioned at different points over an arc of about 200 degrees; with any larger arc the paired extremity, left knee L, blocks the way. Detector 24, smaller than source 22 and typically placed very near subject 20, can be positioned between the patient's right and left knees and is thus capable of positioning over the full circular orbit.

A substantially complete/full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints and other applications. Moreover, there can be diagnostic situations in which obtaining projection images over a certain range of angles has advantages, but patient anatomy blocks the source, detector, or both from imaging over that range. Some of the proposed solutions for obtaining images of extremities under these conditions require the patient to assume a position that is awkward or uncomfortable. The position of the extremity, as imaged, is not representative of how the limb or other extremity serves the patient in movement or under weight-bearing conditions. It can be helpful, for example, to examine the condition of a knee or ankle joint under the normal weight load exerted on that joint by the patient as well as in a relaxed position. But, if the patient is required to assume a position that is not usually encountered in typical movement or posture, there may be excessive strain, or insufficient strain, or poorly directed strain or tension, on the joint. The knee or ankle joint, under some artificially applied load and at an angle not taken when standing, may not behave exactly as it does when bearing the patient's weight in a standing position. Images of extremities under these conditions may fail to accurately represent how an extremity or joint is used and may not provide sufficient information for assessment and treatment planning.

Still other difficulties with conventional solutions for extremity imaging relate to poor image quality. For image quality, the CBCT sequence requires that the detector be positioned close to the subject and that the source of the cone beam radiation be at a sufficient distance from the subject. This provides the best image and reduces image truncation and consequent lost data. Positioning the subject midway between the detector and the source, as some conventional systems have done, not only noticeably compromises image quality, but also places the patient too near the radiation source, so that radiation levels are considerably higher.

CBCT imaging represents a number of challenges that also affect other types of volume imaging that employ a radiation source and detector orbiting an extremity over a range of angles. There are various tomographic imaging modes that can be used to obtain depth information for a scanned extremity.

In summary, for extremity imaging, particularly for imaging the lower paired extremities, a number of improvements are needed, including the following:

(i) improved placement of the radiation source and detector relative to the imaged subject to provide acceptable radiation levels and image quality throughout the scanning sequence, with the capability for at least coarse automated setup for examining an extremity under favorable conditions;

(ii) system flexibility for imaging at different heights with respect to the rotational axis of the source and detector, including the flexibility to allow imaging with the patient standing or seated comfortably, such as with a foot in an elevated position, for example;

(iii) capability to adjust the angle of the rotational axis to suit patient positioning requirements;

(iv) improved patient accessibility, so that the patient does not need to contort, twist, or unduly stress limbs or joints that may have been injured in order to provide images of those body parts;

(v) improved ergonomics for obtaining the CBCT image, allowing the patient to stand or sit with normal posture, for example. This would also allow load-bearing extremities, such as legs, knees, and ankles, to be imaged under the normal load exerted by the patient's weight, rather than under simulated loading conditions and provide options for supporting the patient; and (vi) adaptability for multi-use imaging, allowing a single imaging apparatus to be configurable for imaging any of a number of extremities, including knee, ankle, toe, hand, elbow, and other extremities. This also includes the capability to operate the imaging system in different imaging modes, including CBCT, two-dimensional (2-D) projection radiography, fluoroscopy, and other tomography modes.

The perspective and corresponding top views of FIG. 2 show how the scanning pattern is provided for components of a CBCT imaging apparatus 10 according to an embodiment of the application. A detector path 28 of a suitable radius R1 from a central axis β is provided for a detector device by a detector transport 34. A source path 26 of a second, larger radius R2 is provided for a radiation source by a source transport 32. In one embodiment, a non-linear source path 26 is greater in length than a non-linear detector path 24. According to an embodiment of the application, described in more detail subsequently, the same transport system provides both detector transport 34 and source transport 32. The extremity, subject 20, is preferably substantially centered along central axis β so that central axis β can be considered as a line through points in subject 20. In one embodiment, an imaging bore or the CBCT apparatus can include or encompass the central axis β. The limiting geometry for image capture is due to the arc of source transport 32, blocked by a gap 38 (e.g., for patient anatomy, such as by a paired limb), and thus limited typically to less than about 220 degrees, as noted previously. The circumferential gap or opening 38 can occupy the space between the endpoints of the arc of source path 26. Gap or opening 38 gives space for the patient a place to stand, for example, while one leg is being imaged.

Figure 3A:
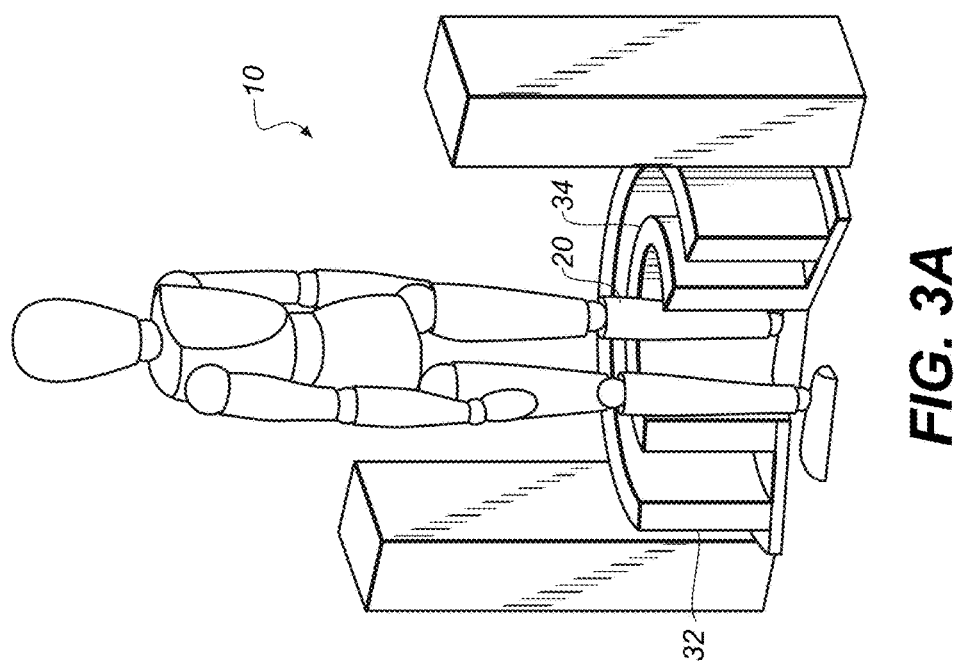
FIG. 3A is a perspective view showing patient access to an imaging apparatus according to an embodiment of the application.
Figure 3B:
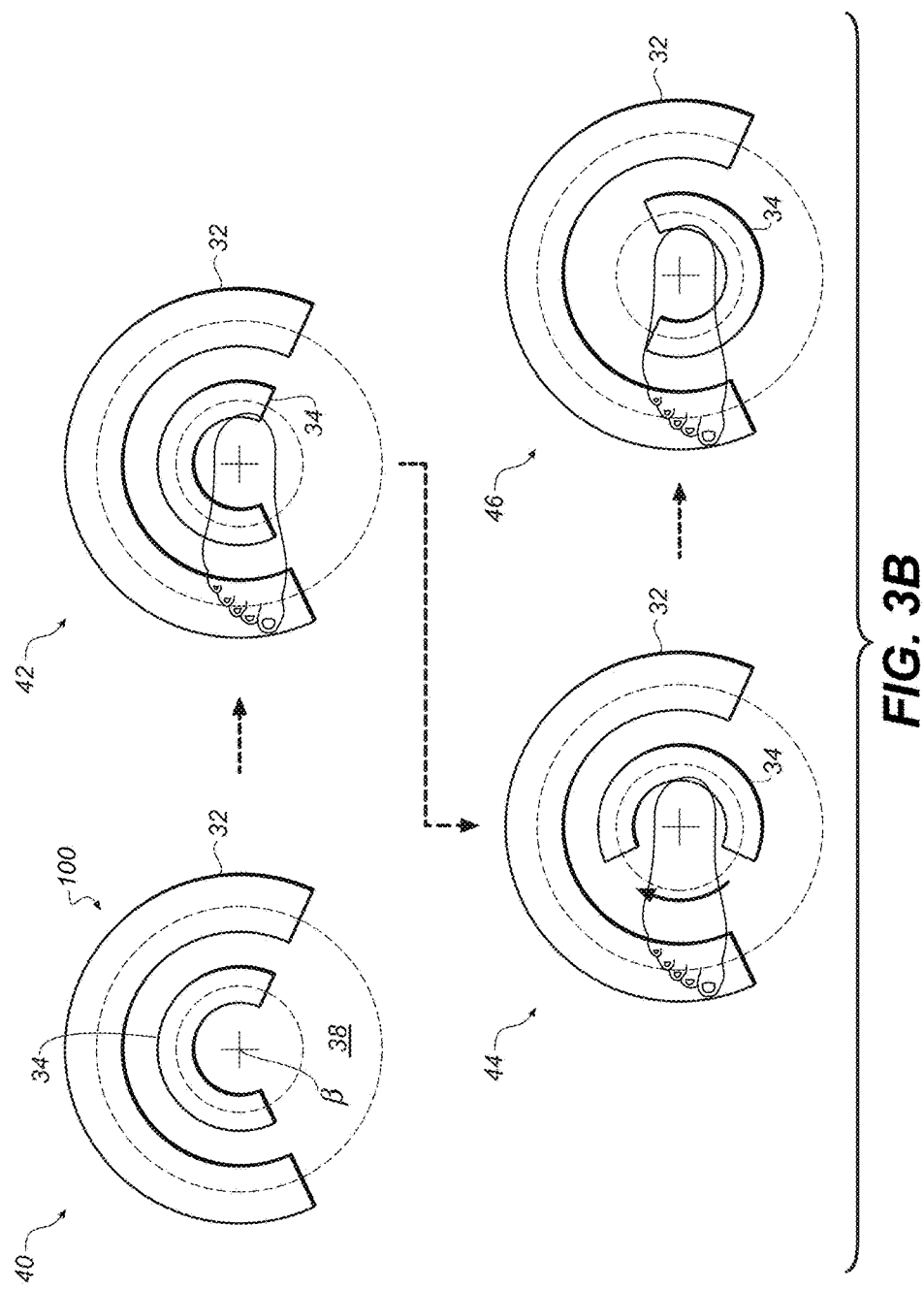
FIG. 3B is a top view showing a sequence of steps for enclosing the extremity to be imaged within the path of the detector transport.

Detector path 28 can extend through circumferential gap 38 to allow scanning, since the detector is not necessarily blocked by patient anatomy but can have a travel path at least partially around an imaged extremity that can extend between the standing patient's legs. Embodiments of the present invention allow temporary restriction of the detector path 28 to allow access for the patient as part of initial patient positioning. The perspective view in FIG. 2, for example, shows detector transport 34 rotated to open up circumferential gap 38 so that it extends from the axis β (e.g., beyond a source path or housing). With detector transport 34 translated to the open position shown in FIG. 3A, the patient can freely move in and out of position for imaging. When the patient is properly in position, detector transport 34 is revolved about axis β by more than 180 degrees; according to an embodiment of the application, detector transport 34 is revolved about axis β by substantially 200 degrees. This patient access and subsequent adjustment of detector transport 34 is shown in successive stages for positions 40, 42, 44, and 46 for apparatus 100 in FIG. 3B. This orbital movement confines the extremity to be imaged more effectively and places detector 24, not visible in FIGS. 2-3B due to the detector transport 34 housing, in position near subject 20 for obtaining the first projection image in sequence. In one embodiment, a detector transport 34 can include shielding or a door over part of the detector path, and/or the gap 38.

Circumferential gap or opening 38 not only allows access for positioning of the subject leg or other extremity, but also allows sufficient space for the patient to stand in normal posture during imaging, placing the subject leg for imaging in the central position along axis β (FIG. 2) and the non-imaged paired leg within the space defined by circumferential gap 38. Circumferential gap or opening 38 extends approximately 180 degrees minus the fan angle (e.g., between ends of the source path), which is determined by source-detector geometry and distance. Circumferential gap or opening 38 permits access of the extremity so that it can be centered in position along central axis β. Once the patient's leg or other extremity is in place, detector transport 34, or a hooded cover or hollow door or other member that defines this transport path, can be revolved into position, closing the detector portion of circumferential gap or opening 38.

Figure 4:
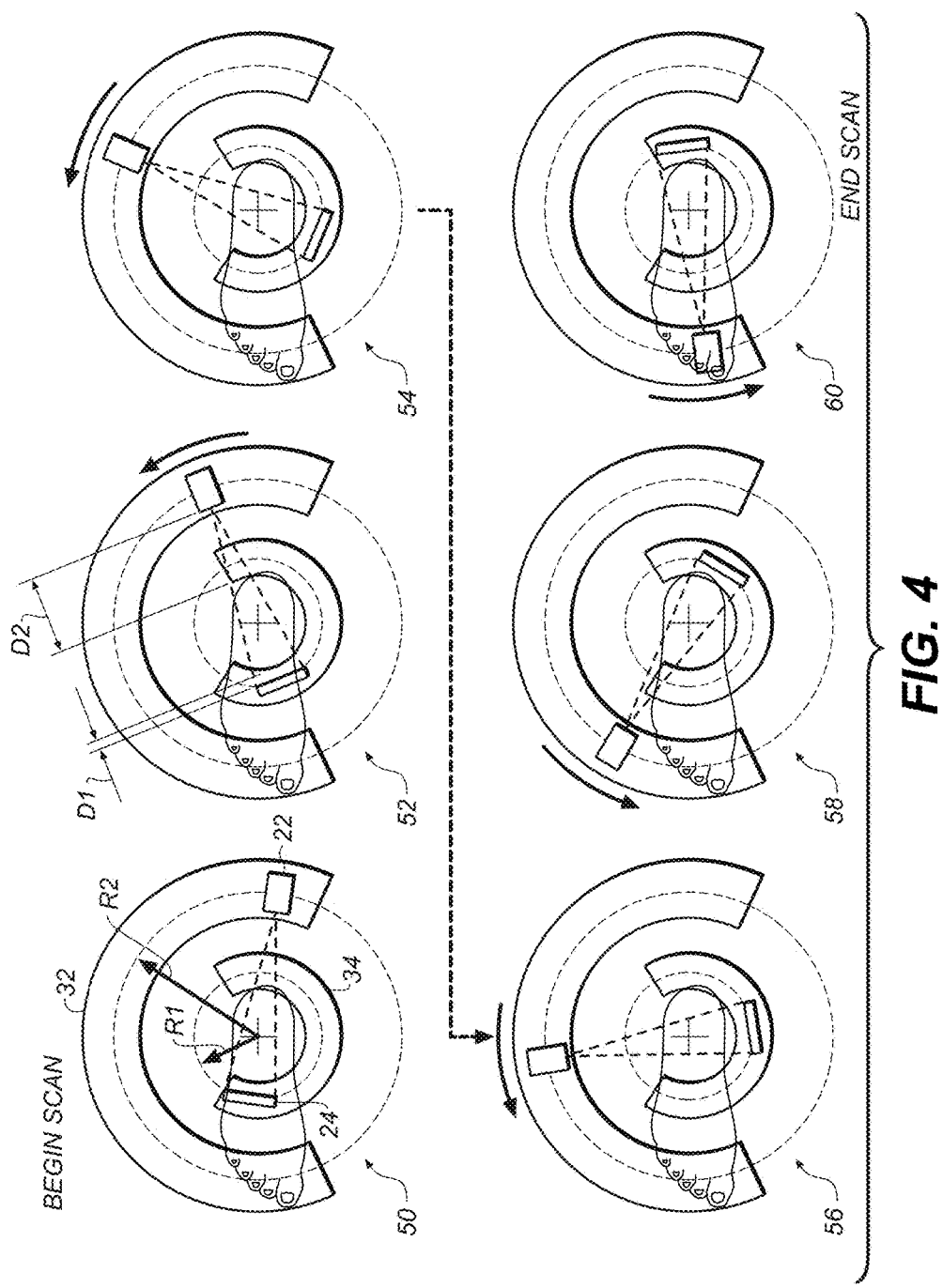
FIG. 4 show portions of the operational sequence for obtaining CBCT projections of a portion of a patient's leg at a number of angular positions when using the imaging apparatus according to an embodiment of the application.

By way of example, the top views of FIG. 4 show portions of the operational sequence for obtaining CBCT projections of a portion of a patient's leg at a number of angular positions when using a CBCT imaging apparatus. The relative positions of radiation source 22 and detector 24, which may be concealed under a hood or chassis, as noted earlier, are shown in FIG. 4. The source 22 and detector 24 can be aligned so the radiation source 22 can direct radiation toward the detector 24 (e.g., diametrically opposite) at each position during the CBCT scan and projection imaging. The sequence begins at a begin scan position 50, with radiation source 22 and detector 24 at initial positions to obtain an image at a first angle. Then, both radiation source 22 and detector 24 revolve about axis β as represented in interim scan positions 52, 54, 56, and 58. Imaging terminates at an end scan position 60. As this sequence shows, source 22 and detector 24 are in opposing positions relative to subject 20 at each imaging angle. Throughout the scanning cycle, detector 24 is within a short distance D1 of subject 20. Source 22 is positioned beyond a longer distance D2 of subject 20. The positioning of source 22 and detector 24 components on each path can be carried out by separate actuators, one for each transport path, or by a single rotatable member, as described in more detail subsequently. It should be noted that scanning motion in the opposite direction, that is, clockwise with respect to the example shown in FIG. 4, is also possible, with the corresponding changes in initial and terminal scan positions.

Figure 5:
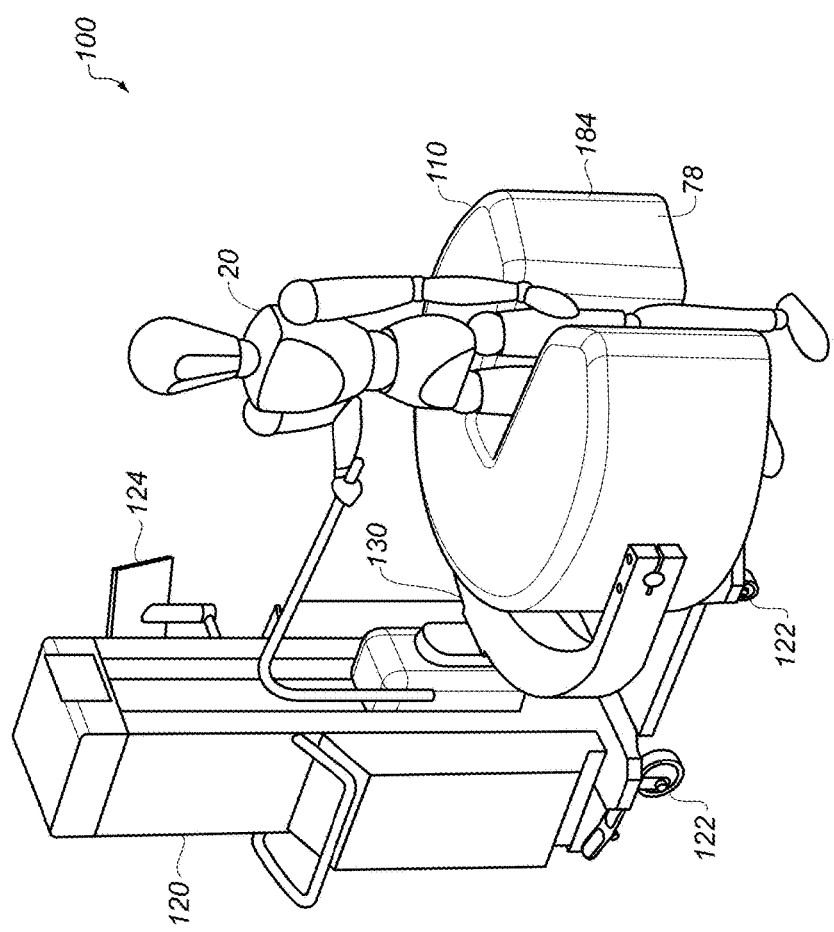
FIG. 5 is a perspective view that shows a CBCT imaging apparatus for extremity imaging according to an embodiment of the application.
Figure 6C:
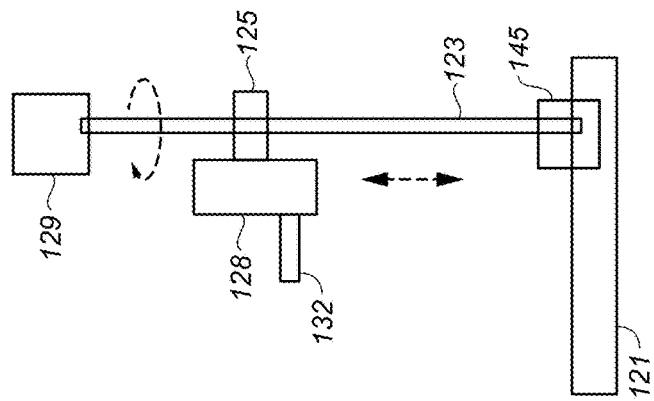
FIG. 6C is a schematic diagram that shows components of the positioning system for the imaging scanner.

Given this operation sequence in which the source 22 and detector 24 orbit the extremity, the usefulness of an imaging system that is adaptable for imaging patient extremities with the patient sitting or standing and in load-bearing or non load-bearing postures can be appreciated. The perspective view of FIG. 5 shows a CBCT imaging apparatus 100 for extremity imaging according to an embodiment of the application. Imaging apparatus 100 has a gimbaled imaging ring or scanner 110 that houses and conceals source 22 and detector 24 within a housing 78 with a cover 184. FIG. 5 shows their supporting transport mechanisms. Scanner 110 is adjustable in height and rotatable in gimbaled fashion about non-parallel axes, such as about substantially orthogonal axes as described in subsequent figures, to adapt to various patient postures and extremity imaging conditions. A support column 120 supports scanner 110 on a yoke, or bifurcated or forked support arm 130, a rigid supporting element that has adjustable height and further provides rotation of scanner 110 as described subsequently. Support column 120 can be fixed in position, such as mounted to a floor, wall, or ceiling. According to portable CBCT embodiments such as shown in FIG. 6A and elsewhere, support column 120 mounts to a support base 121 that also includes optional wheels or casters 122 for transporting and maneuvering imaging apparatus 100 into position. A control panel 124 can provide an operator interface, such as a display monitor, for entering instructions for apparatus 100 adjustment and operation. Support column 120 can be of fixed height or may have telescoping operation, such as for improved visibility when apparatus 100 is moved.

Vertical and Rotational Movement

FIG. 6A shows portions of exemplary internal imaging and positioning mechanisms (with covers removed) for scanner 110 that allow imaging apparatus 100 the capability for imaging extremities with a variety of configurations. FIG. 6B shows rotation axes definitions for scanner 110 positioning. The α-axis and the γ-axis are non-parallel, to allow gimbaled action. According to an embodiment of the applications shown in FIG. 6A, the α-axis and the γ-axis are mutually orthogonal. The α-axis is substantially orthogonal to the z-axis. The intersection of the α-axis and the γ-axis can be offset from support column 120 by some non-zero distance.

First considering the z-axis, FIG. 6A shows an exemplary embodiment to achieve vertical motion. Within support column 120, a vertical carriage translation element 128 is actuated in order to travel upwards or downwards along column 120 within a track 112 in a vertical direction. Carriage translation element 128 has a support shaft 132 that is coupled to an actuator 136 for providing α-axis rotation to forked or C-shaped support arm 130. Forked support arm 130, shown only partially in FIG. 6A to allow a better view of underlying components, is coupled to support shaft 132. X-ray source 22 and receiver 24 are mounted on a rotatable gantry 36 for rotation about a scan or central axis, designated as the β axis. Axis β is orthogonal to the α-axis and the γ-axis.

Figure 6D:
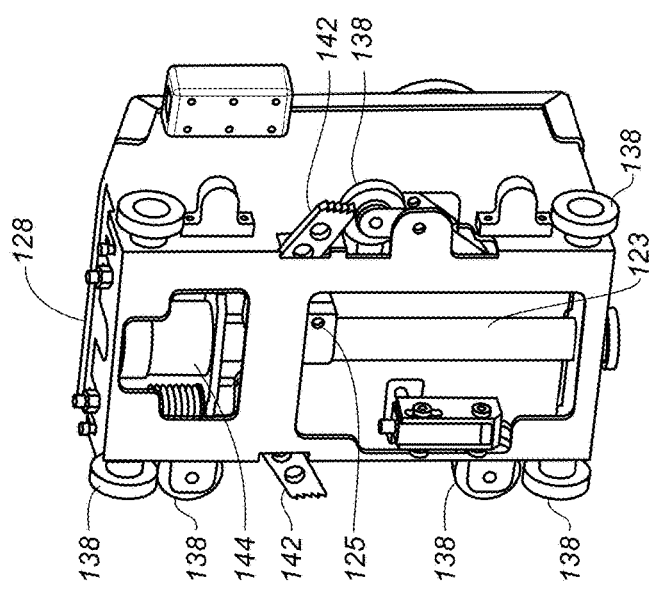
FIG. 6D is a perspective view showing some of the components of a vertical translation apparatus.

It can be appreciated that z-axis translation can be effected in a number of ways. Challenges that must be addressed by the type of system that is used include handling the weight of forked support arm 130 and the imaging scanner 110 that arm 130 supports. This can easily weigh a few hundred pounds. In addition, precautions must be provided for handling conditions such as power loss, contact with the patient, or mechanical problems that hamper positioning movement or operation. According to an embodiment of the application, as shown schematically in FIG. 6C and in the perspective view of FIG. 6D, a vertical actuator 129 rotates a threaded shaft 123. Vertical carriage translation element 128 employs a ball screw mount apparatus 125 to translate rotational motion to the needed linear (e.g., z-direction) motion, thus urging vertical carriage translation element 128 upward or allowing vertical carriage translation element 128 to move downward. Ball screw translation devices are advantaged for handling high weight loads and are typically more efficient than other types of translators using threaded devices. The use of a ball screw arrangement also allows a small motor to drive the shaft that lifts scanner 110 into position and can help to eliminate the need for a complex and bulky counterweight system for allowing control of vertical movement. An encoder 145, such as a linear encoder element, can provide feedback signals that are used to indicate the vertical position of vertical carriage translation element 128.

Vertical carriage translation element 128 travels inside track 112 formed in support column 120 (FIG. 6A); wheels 138 help to guide translation element 128 within the slots. Paired wheels 138 can be orthogonal to each other to provide centering within column 120.

A braking system can also be provided for support column 120. Spring-loaded brakes 142 (FIG. 6D) are positioned to actuate and grip shaft 123 or other mechanical support when mechanical difficulties, power failure, or other conditions are detected. A sensor 144, such as a load cell, is configured to sense rapid movement or interference conditions that are undesirable and to cause brake 142 actuation.

Other features of support column 120 for vertical translation include built-in redundancy, with springs to absorb weight and impact, the load cell to sense a mechanical problem including obstruction by the patient, and manually operable brake mechanisms.

It should be noted that other types of translation apparatus could be used for providing vertical movement of vertical carriage translation element 128. One conventional method for vertical movement control uses a system of pulleys and counterweights to provide lifting force, with motorized assistance. Such an arrangement, however, can be disadvantageous because it can add considerable weight to the column 120 and supporting structure. In spite of its weight-related drawbacks, use of a pulley mechanism can be advantageous for allowing a retractable or telescoping column 120 arrangement, for example, to simplify transport of imaging apparatus 100 between rooms.

Gimbaled Arrangement for Scanner

Forked support arm 130 can support scanner 110 in a gimbaled arrangement. Source 22 and detector 24 are shown on gantry 36 for reference in FIG. 6A and covered in the alternate view of FIG. 6E. Vertical carriage translation element 128 is configured to ride within a track 112 (FIG. 6A) within support column 120.

For certain exemplary embodiments, some level of manual operability can be provided, such as for power loss situations. In one embodiment, forked support arm 130 can be lifted upwards in position by one or more persons, for example, raising vertical carriage translation element 128 even when brakes 142 are set. Shifting support arm 130 upwards does not release the brakes 142, but simply sets the brakes 142 to hold element 128 position at new levels.

According to an alternate embodiment of the application, vertical carriage translation element 128 can be a motor that moves vertically along supporting threaded shaft 132; alternately, vertical carriage translation element 128 can be driven using a chain, pulley, or other intermediate mechanism that has considerable counterweights for manually raising and lowering vertical carriage translation element 128 and its connected forked support arm 130 and components within support column 120. Additional supporting components include a more complex braking system, such as a pneumatic braking system for providing a force opposing gravity in order to prevent sudden movement of forked support arm 130 as a precaution against damage or injury. Vertical carriage translation element 128 can be automated or may be a manually operated positioning device that uses one or more springs or counterweight devices to allow ease of manual movement of forked support arm 130 into position.

Next, considering the α-axis movement of forked support arm 130, in one embodiment a rotational actuator 136 can be energizable to allow rotation of shaft 132 (FIG. 6A). This rotational actuation can be concurrent with z-axis translation as well as with rotation with respect to the γ-axis.

Figure 6E:
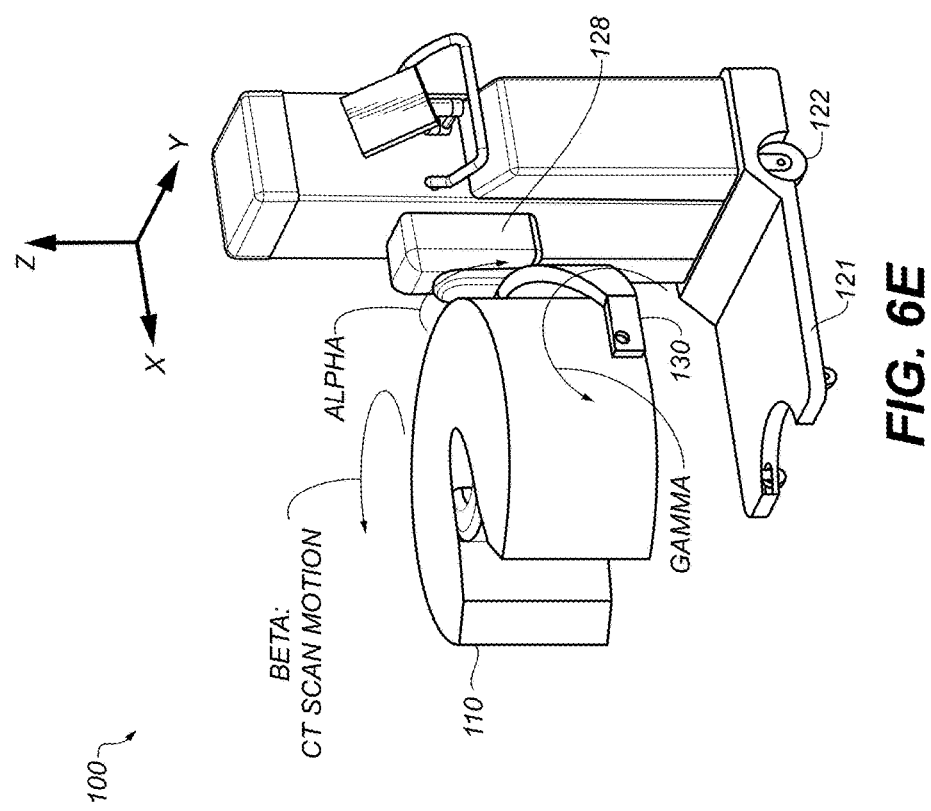
FIG. 6E shows the CBCT imaging apparatus with covers installed.

Forked support arm 130 allows movement relative to the γ-axis according to the position and angle of forked support arm 130. In the example of FIG. 6A, the γ-axis is oriented vertically, substantially in parallel with the z-axis. FIG. 6E shows the γ-axis oriented horizontally. A pivoting mount 140 with a rotational actuator 146, provided by forked support arm 130, allows rotation along the γ-axis. The gimbaled combination of α-axis and γ-axis rotation can allow the imaging apparatus to be set up for imaging in a number of possible positions, with the patient standing, seated, or prone.

Figure 7B:
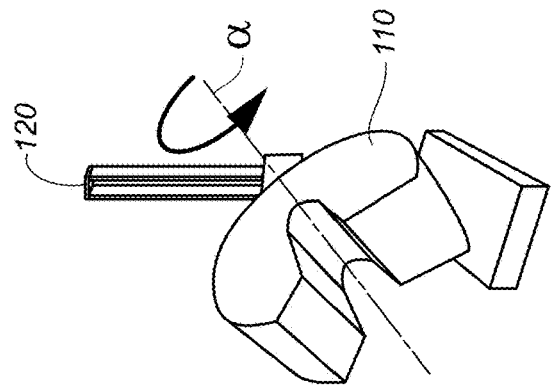
FIG. 7B shows rotation of the imaging ring about an α-axis that is orthogonal to the z-axis.
Figure 7A:
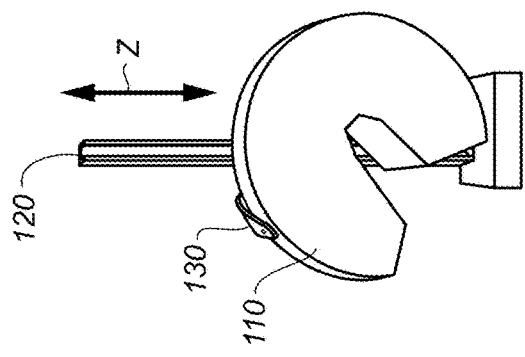
FIG. 7A shows translation of the imaging ring with respect to a vertical or z-axis.
Figure 7C:
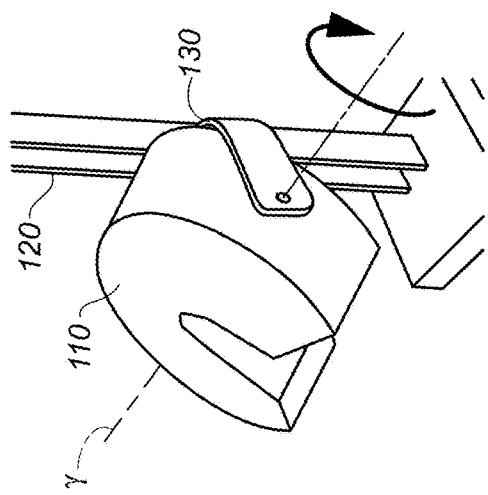
FIG. 7C shows rotation of the imaging ring about a γ-axis that is orthogonal to the α-axis.

An exemplary positioning capability of the imaging apparatus 100 is shown n FIGS. 7A-7C. FIG. 7A shows movement of forked support arm 130 on support column 120 to provide z-axis (vertical) translation of scanner 110. FIG. 7B shows rotation of forked support arm 130 about the horizontal α-axis. FIG. 7C shows rotation about the γ-axis as defined by the C-arm arrangement of forked support arm 130.

Sequence and Controls for Positioning Support Arm 130

According to an embodiment of the present disclosure, an initial set of operator commands automatically configure CBCT imaging apparatus 100 to one of a well-defined set of default positions for imaging, such as those described subsequently. The patient waits until this initial setup is completed. Then, the patient is positioned at CBCT imaging apparatus 100 and any needed adjustments in height (z-axis) or rotation about the α or γ axes can be made by the technician. This type of fine-tuning adjustment is at slow speeds for increased patient comfort and because only incremental changes to position are needed in most cases.

Figure 7E:
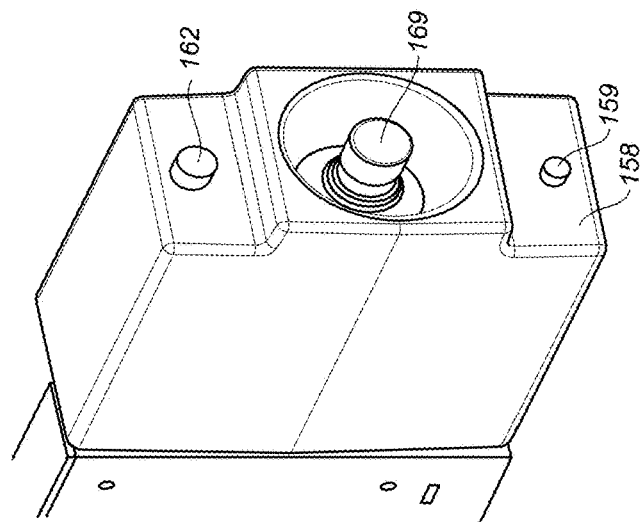
FIG. 7E shows an enlarged view of the positioning controls.
Figure 7D:
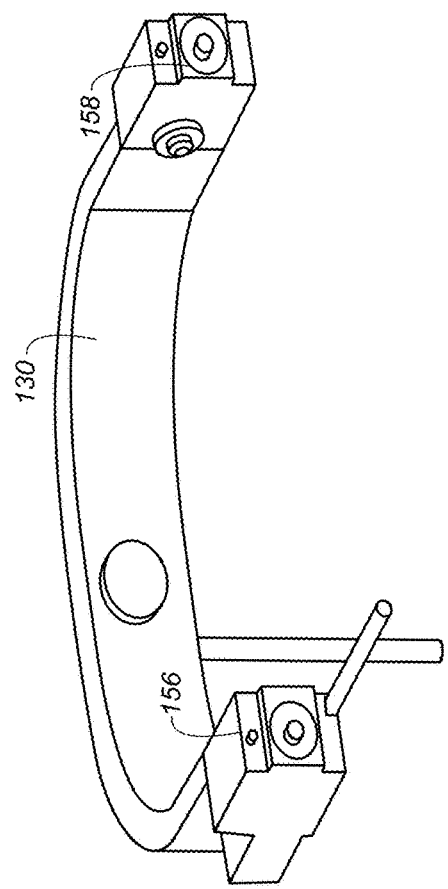
FIG. 7D shows the position of operator controls for fine-tune position of the imaging scanner.

FIG. 7D and the enlarged view of FIG. 7E show user control stations 156, 158 that are provided on arm 130 (with scanner 110 removed for improved visibility) for operator adjustment of z-axis translation and α- and γ-axis rotation as described in FIGS. 7A-7C. Both control stations 156 and 158 are essentially the same, duplicated to allow easier access for the operator for different extremity imaging arrangements. By way of example, FIG. 7E shows an enlarged view of control station 158. An enablement switch 159 is pressed to activate a control 169 and an associated indicator illuminates when control 169 is active or enabled. As a patient safety feature to protect from inadvertent patient contact with the controls in some imaging configurations, one or both control stations 156, 158 are disabled. One or both control stations 156, 158 can also be disabled following a time-out period after switch 159 has been pressed. An emergency stop control 162 can stop all motion of the imaging apparatus including downward motion of support arm 130.

Still referring to FIG. 7E, control 169 can activate any of the appropriate actuators for z-axis translation, α-axis rotation and/or γ-axis rotation. Exemplary responses of the system can be based on operator action, as follows:

(i) z-axis vertical movement is effected by pressing control 169 in a vertical upward or downward direction. The control logic adjusts for the angular position of the support arm 130, so that pressing the control upward provides z-axis movement regardless of support arm 130 orientation.

(ii) α-axis rotation is effected by rotating control 169. Circular motion of control 60 in an either clockwise (CW) or counterclockwise (CCW) direction causes corresponding rotation about the α axis.

(iii) γ-axis rotation is effected by horizontal left-to-right or right-to-left movement of control 169. As with z-axis movement, control logic adjusts for the angular position of the support arm 130, so that left-right or right-left movement is relative to the operator regardless of support arm 130 orientation.

It should be noted that CBCT imaging apparatus 100 as shown in FIG. 6E provides three degrees of freedom (DOF) for scanner 110 positioning. In addition to the z-axis translation and rotation about α- and γ-axes previously described, casters 122 allow rotation of scanner 110 position with respect to the z-axis as well as translation along the floor.

Configurations for Imaging Various Extremities

Given the basic structure described with reference to FIGS. 6A-7D, the positioning versatility of scanner 110 for various purposes can be appreciated. FIGS. 8-14 show, by way of example, how this arrangement serves different configurations for extremity imaging.

Figure 8:
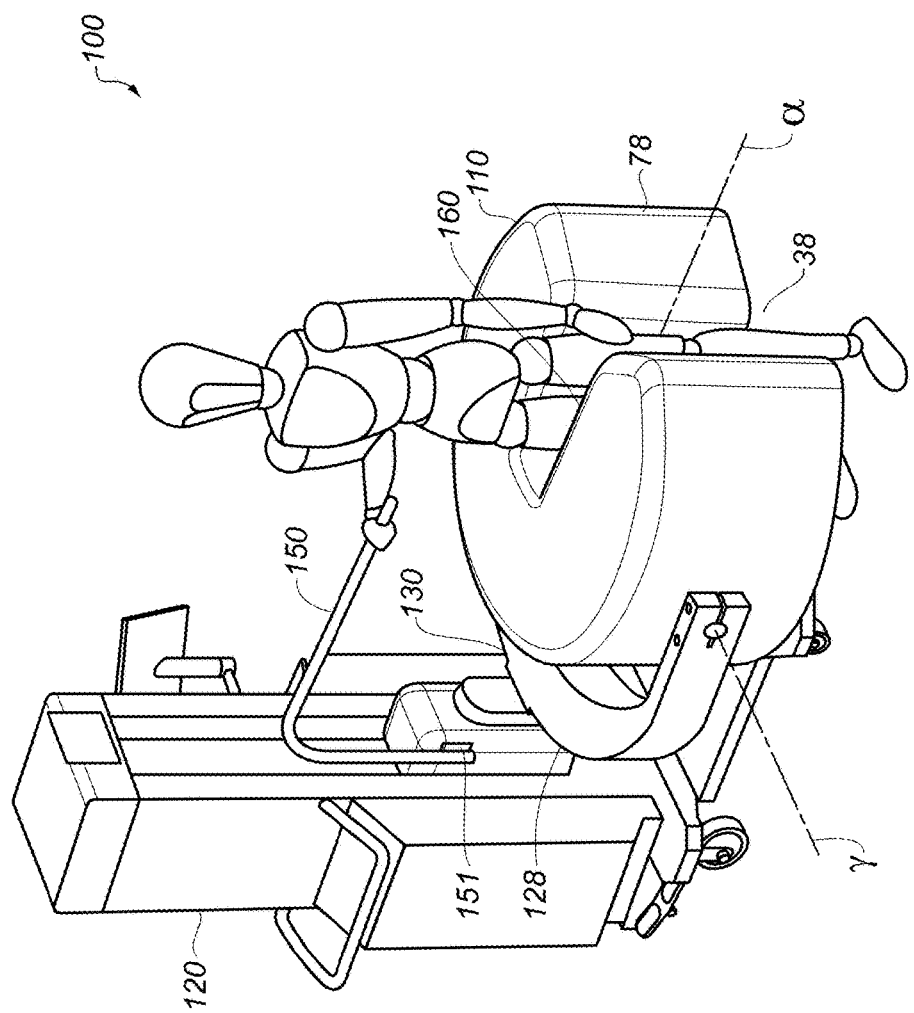
FIG. 8 is a perspective view that shows the extremity imaging apparatus configured for knee imaging with a standing patient.

FIG. 8 shows an exemplary scanner 110 positioning for a knee exam, where subject 20 is a standing patient. An optional patient support bar 150 can be attached to support column 120. In one embodiment, support bar 150 is mounted to vertical carriage translation element 128. Accordingly, as the vertical carriage translation element 128 moves, a corresponding position of the support bar 150 can be moved. According to an alternate embodiment of the application, the support bar 150 can be mounted to the scanner 110, such as to the cover of scanner 110 or to the forked support arm 130. In contrast, embodiments of support bar 150 can be motionless during imaging or during a scan by the scanner 110. For this embodiment, vertical adjustment along the z-axis sets the knee of the patient at the center of the scanner 110. Forked support arm 130 is arranged so that the plane that contains both the α-axis and the γ-axis is substantially horizontal. Patient access is through an opening, circumferential gap or opening 38 in scanner 110. A door 160 is pivoted into place across gap 38 to enclose an inner portion of circumferential gap or opening 38. Door 160 fits between the legs of the patient once the knee of the patient is positioned.

Figure 9:
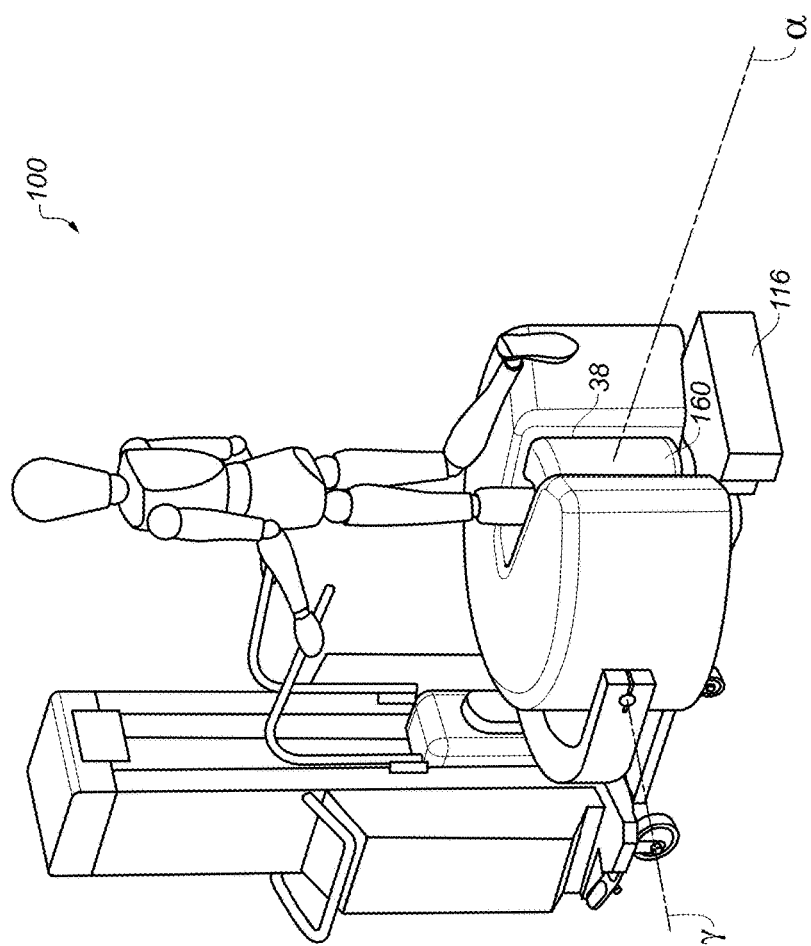
FIG. 9 is a perspective view that shows the extremity imaging apparatus configured for foot or ankle imaging with a standing patient.

Certain exemplary embodiments of optional patient support bar 150 can be mounted to movable portions of the CBCT apparatus 100, preferably to have a prescribed spatial relationship to an imaging volume. For such embodiments, a presence detector 151 can be configured to detect when the support bar 150 is mounted to the CBCT system 100. When detected, a controller or the like, for example, in the control panel 124, can calculate scanner 110, and/or forked support arm 130 movements to prevent collisions therebetween with the affixed support bar 150. Thus, when attached support bar 150 can limit motion of the scanner 110. Exemplary presence detectors 151 can include but are not limited to magnetic detectors, optical detectors, electro-mechanical detectors or the like. As shown in FIG. 9, a pair of optional or removable support arms 150 can be affixed to the vertical carriage translation element 128 and have their attachment reported by a pair of presence detectors 151.

For FIG. 8 and selected subsequent embodiments, door 160, once pivoted into its closed position, can effectively extend the imaging path by protecting and/or providing the curved detector transport 34 path as shown in FIG. 4. With this arrangement, when door 160 is closed to protect the transport path, the knee can be examined under weight-bearing or non-weight-bearing conditions. By enclosing the portion of detector transport 34 path that crosses opening 38, door 160 enables the extremity to be positioned suitably for 3D imaging and to be maintained in position between the source and detector as these imaging components orbit the extremity in the CBCT image capture sequence.

FIG. 9 shows scanner 110 positioning for a foot or ankle exam wherein subject 20 is a standing patient. With this configuration, scanner 110 is lowered to more effectively scan the area of interest. The plane that contains both the α-axis and the γ-axis is approximately 10 degrees offset from horizontal, rotated about the γ axis. A step 116 is provided across circumferential gap or opening 38 for patient access.

Figure 10:
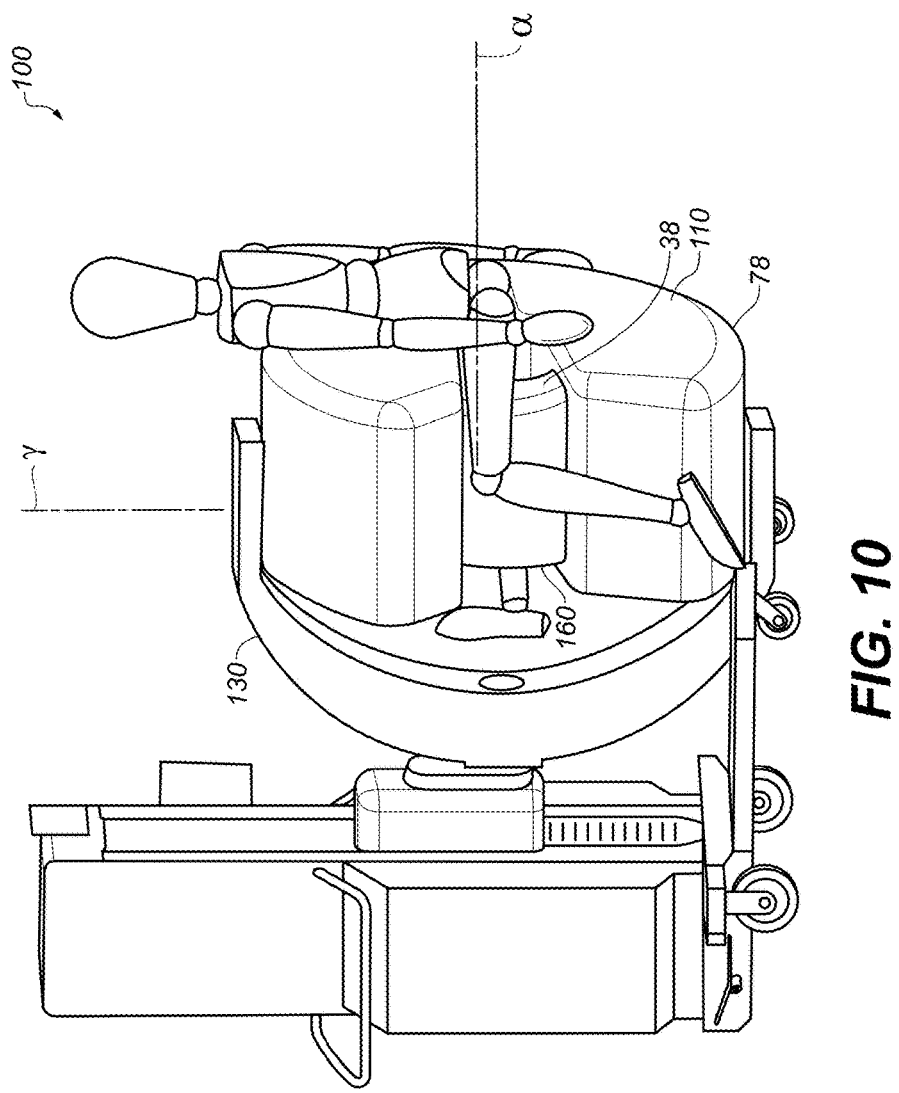
FIG. 10 is a perspective view that shows the extremity imaging apparatus configured for knee imaging with a seated patient.

FIG. 10 shows scanner 110 positioning for a knee exam with the patient seated. For this configuration, forked support arm 130 is elevated with respect to the z-axis. Rotation about the α-axis orients the γ-axis so that it is vertical or nearly vertical. Circumferential gap or opening 38 is positioned to allow easy patient access for imaging the right knee. It should be noted that 180 degree rotation about the γ-axis would position circumferential gap or opening 38 on the other side of scanner 110 and allow imaging of the other (left) knee.

Figure 11:
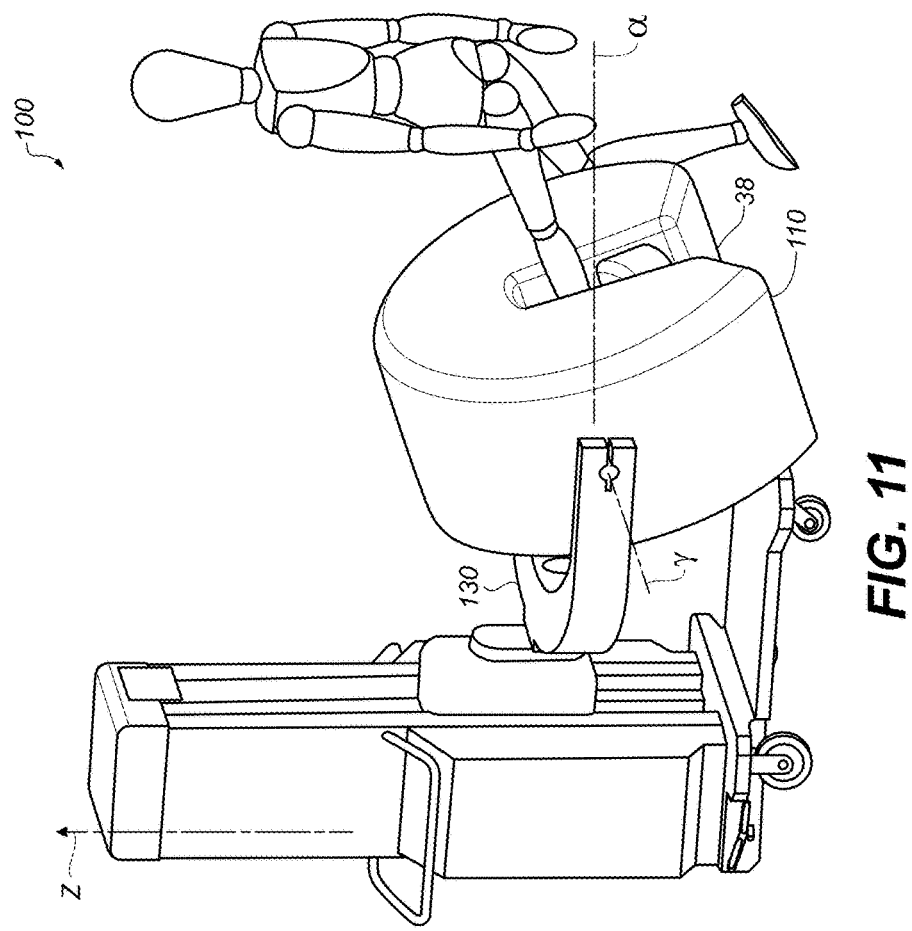
FIG. 11 is a perspective view that shows the extremity imaging apparatus configured for foot or ankle imaging with a seated patient.

FIG. 11 shows scanner 110 positioning for a foot or ankle exam with the patient seated. For this configuration, forked support arm 130 is elevated with respect to the z-axis. Some slight rotation about the α-axis may be useful. Rotation about the γ-axis orients scanner 110 at a suitable angle for imaging. Circumferential gap or opening 38 is positioned for comfortable patient access.

Figure 12:
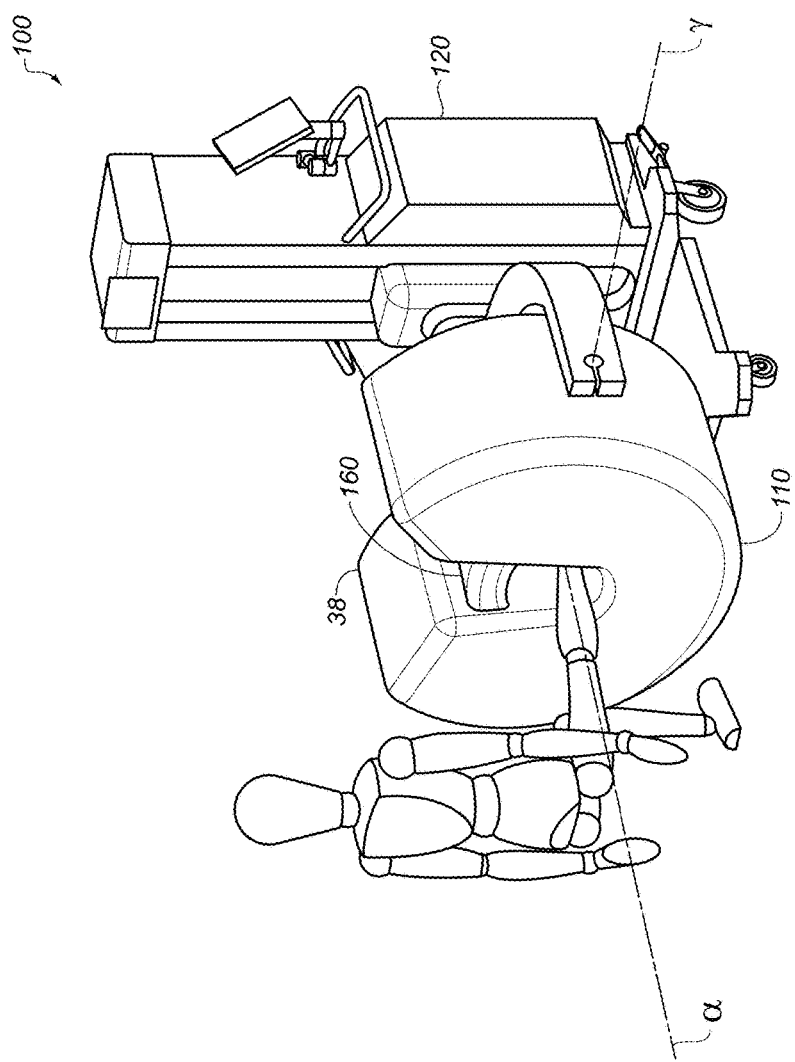
FIG. 12 is a perspective view that shows the extremity imaging apparatus configured for toe imaging with a seated patient.

FIG. 12 shows scanner 110 positioning for a toe exam with the patient seated. For this configuration, forked support arm 130 is elevated with respect to the z-axis. Rotation about the γ-axis positions circumferential gap 38 at the top of the unit for patient access.

Figure 13:
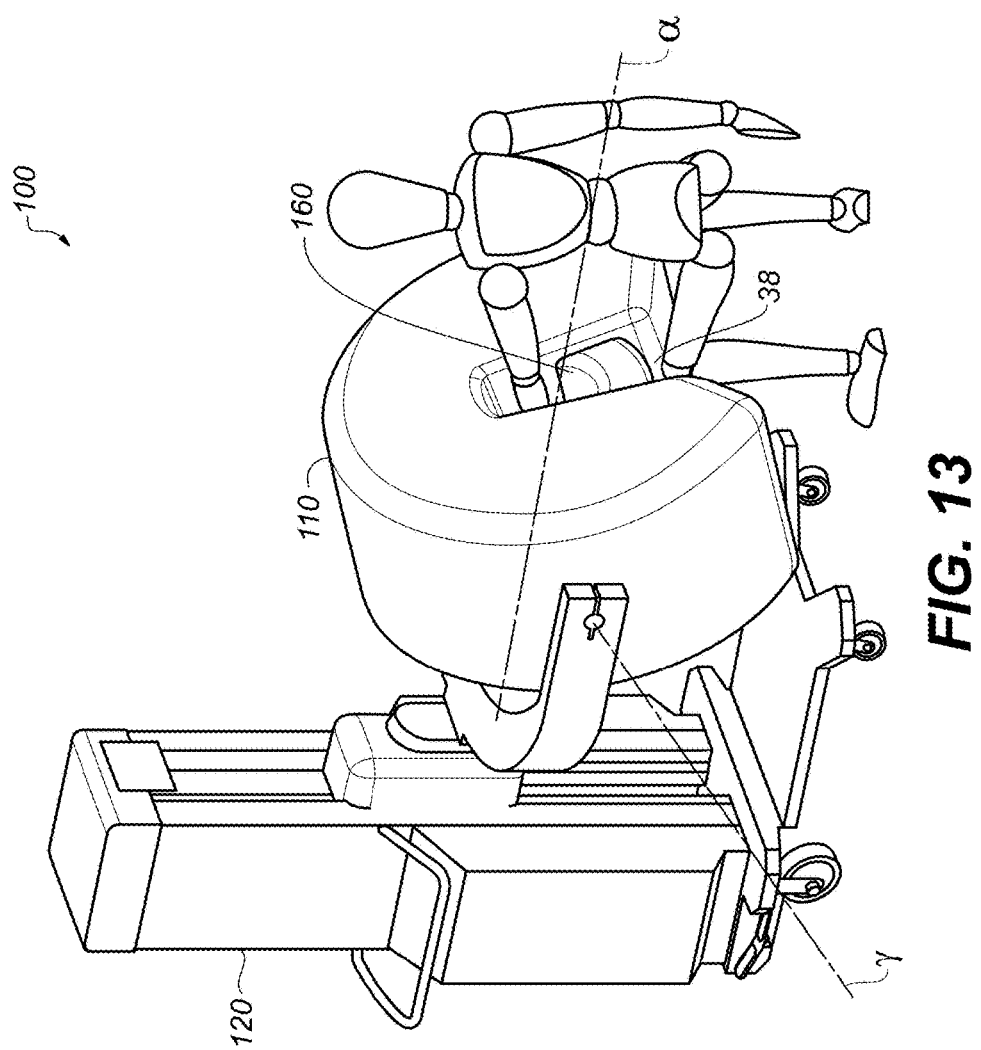
FIG. 13 is a perspective view that shows the extremity imaging apparatus configured for hand imaging with a seated patient.

FIG. 13 shows scanner 110 positioning for a hand exam, with the patient seated. For this configuration, forked support arm 130 is elevated with respect to the z-axis. Rotation about the γ-axis positions circumferential gap 38 suitably for patient access. Rotation about the α-axis may be provided to orient scanner 110 for patient comfort.

Figure 14:
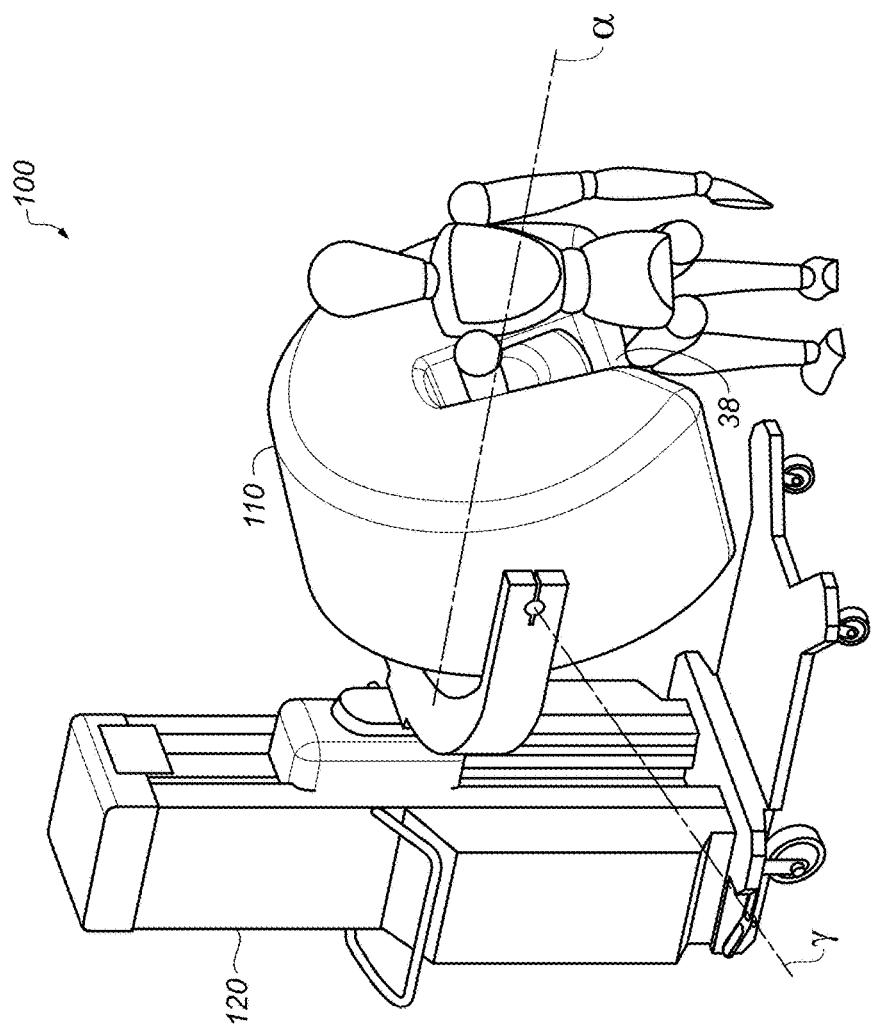
FIG. 14 is a perspective view that shows the extremity imaging apparatus configured for elbow imaging with a seated patient.

FIG. 14 shows scanner 110 positioning for an elbow exam, with the patient seated. For this configuration, forked support arm 130 is again elevated with respect to the z-axis. Rotation about the γ-axis positions circumferential gap 38 suitably for patient access. Further rotation about the α-axis may be provided for patient comfort.

In one embodiment of CBCT imaging apparatus 100, the operator can first enter an instruction at the control console or control panel 124 (FIG. 5) that specifies the exam type (e.g., for the configurations shown in FIGS. 8-14). The system then automatically adapts the chosen configuration, prior to positioning the patient. Once the patient is in place, manually controlled adjustments to z-axis and α- and γ-axes rotations can be made, as described previously.

Scanner Configuration and Operation

As previously described with reference to FIGS. 1-4, scanner 110 is configured to provide suitable travel paths for radiation source 22 and detector 24 about the extremity that is to be imaged, such as those shown in FIGS. 8-14. Scanner 110 operation in such various exemplary configurations can present a number of requirements that can be at least somewhat in conflict, including the following:

(i) Imaging over a large range of angles, preferably over an arc exceeding 180 degrees plus the fan angle of the radiation source.

(ii) Ease of patient access and extremity positioning for a wide range of limbs.

(iii) Capability to allow both weight-bearing and non-weight-bearing postures that allow imaging with minimized strain on the patient.

(iii) Enclosure to prevent inadvertent patient contact with moving parts.

(iv) Fixed registration of source to detector throughout the scan cycle.

The top view of FIG. 15A shows a configuration of components of scanner 110 that orbit subject 20 according to an embodiment of the application. One or more sources 22 and detector 24 are mounted in a cantilevered C-shaped gantry 36 that is part of a transport assembly 170 that can be controllably revolved (e.g., rotatable over an arc about a central axis β). Source 22 and detector 24 are thus fixed relative to each other throughout their movement cycle. An actuator 172 is mounted to a frame 174 of assembly 170 and provides a moving hinge for gantry pivoting. Actuator 172 is energizable to move gantry 36 and frame 174 with clockwise (CW) or counterclockwise (CCW) rotation as needed for the scan sequence. Housing 184 can reduce or keeps out dust and debris and/or better protect the operator and patient from contact with moving parts.

Figure 15B:
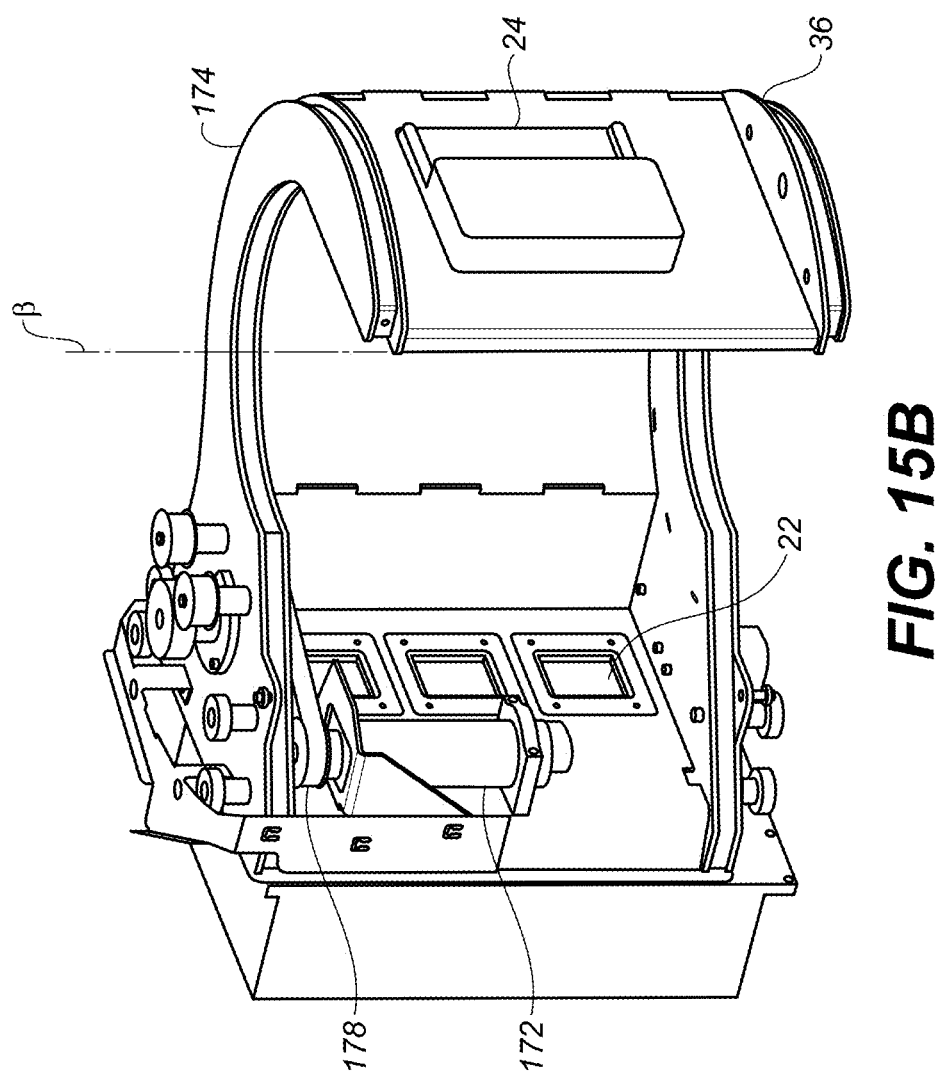
FIG. 15B is a perspective view of a frame that supports scanner components of an extremity imaging apparatus according to an embodiment of the application.

The perspective view of FIG. 15B shows frame 174 and gantry 36 of transport assembly 170 in added detail. Actuator 172 cooperates with a belt 178 to pivot frame 174 for moving source 22 and detector 24 about axis β. The perspective view of FIG. 15C shows frame 174 with added counterweights 182 for improved balance of the cantilevered arrangement.

Figure 16C:
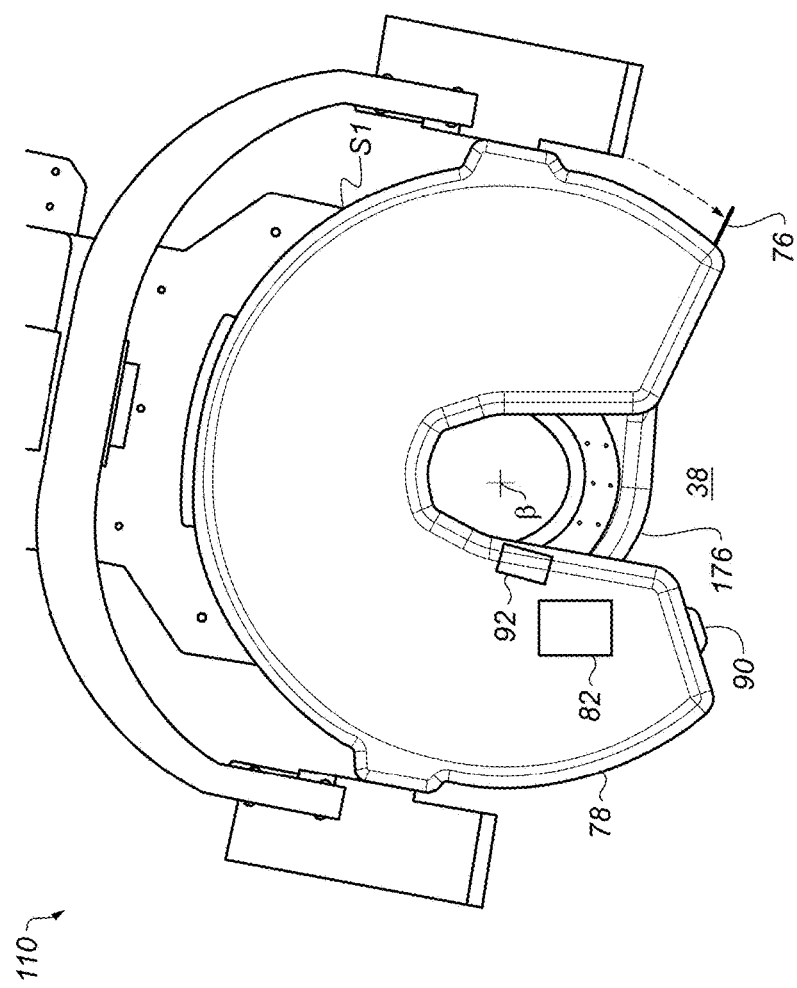
FIG. 16C is a top view of the imaging scanner showing the door closed position.

Because a portion of the scan arc that is detector path 28 (FIG. 2) passes through the circumferential gap or opening 38 that allows patient access, this portion of the scan path should be isolated from the patient. FIGS. 16A, 16B, and 16C show, in successive positions for closing over gap or opening 38, a slidable door 176 that is stored in a retracted position within a housing 180 for providing a covering over the detector path 28 once the patient is in proper position. In one embodiment, door 176 can be substantially a hollow structure that, when closed, allows passage of the detector 24 around the patient's extremity. Referring to FIG. 15B, the portion of frame 174 of gantry 36 that supports detector 24 can pass through the hollow inner chamber provided by door 176 during the imaging scan. At the conclusion of the imaging sequence, frame 174 of gantry 36 rotates back into its home position and door 176 is retracted to its original position for patient access or egress within housing 180. In one embodiment, the door 176 is manually opened and closed by the operator. In one embodiment, interlocks are provided so that movement of scanning transport components (rotation of cantilevered frame 174) is only possible while full closure of the door 176 is sensed.

FIG. 16B also shows top and bottom surfaces 190 and 192, respectively, of housing 180. An outer circumferential surface 194 extends between and connects top and bottom surfaces 190 and 192. An inner circumferential surface 196 is configured to connect the top and bottom surfaces 190 and 192 to form a central opening 198 extending from the first surface to the second surface, where the central opening 198 surrounds the β axis.

As shown with respect to FIGS. 2 and 4, in one embodiment radiation source 22 and detector 24 each can orbit the subject along an arc with radii R2 and R1, respectively. According to an alternate embodiment, within source transport 32, a source actuator could be used, cooperating with a separate, complementary detector actuator that is part of detector transport 34. Thus, two independent actuator devices, one in each transport assembly, can be separately controlled and coordinated by an external logic controller to move source 22 and detector 24 along their respective arcs, in unison, about subject 20.

In the context of the present disclosure, a surface is considered to be "substantially" flat if it has a radius of curvature that exceeds about 10 feet.

The perspective view of FIG. 10 shows the extremity CBCT imaging apparatus 100 configured for knee imaging with a seated patient. From FIG. 10, it can be seen that the patient needs room outside of the scan volume for comfortable placement of the leg that is not being imaged. For this purpose, housing 78 is shaped to provide additional clearance.

As is illustrated in FIGS. 8-14 and 16A-16D, imaging scanner 110 has a housing 78. According to one embodiment of the application, housing 78 is substantially cylindrical; however, a cylindrical surface shape for housing 78 is not required. By substantially cylindrical is meant that, to at least a first approximation, the housing 78 surface shape closely approximates a cylinder, with some divergence from strict geometric definition of a cylinder and with a peripherally gap and some additional features for attachment and component interface that are not in themselves cylindrical.

Figure 17A:
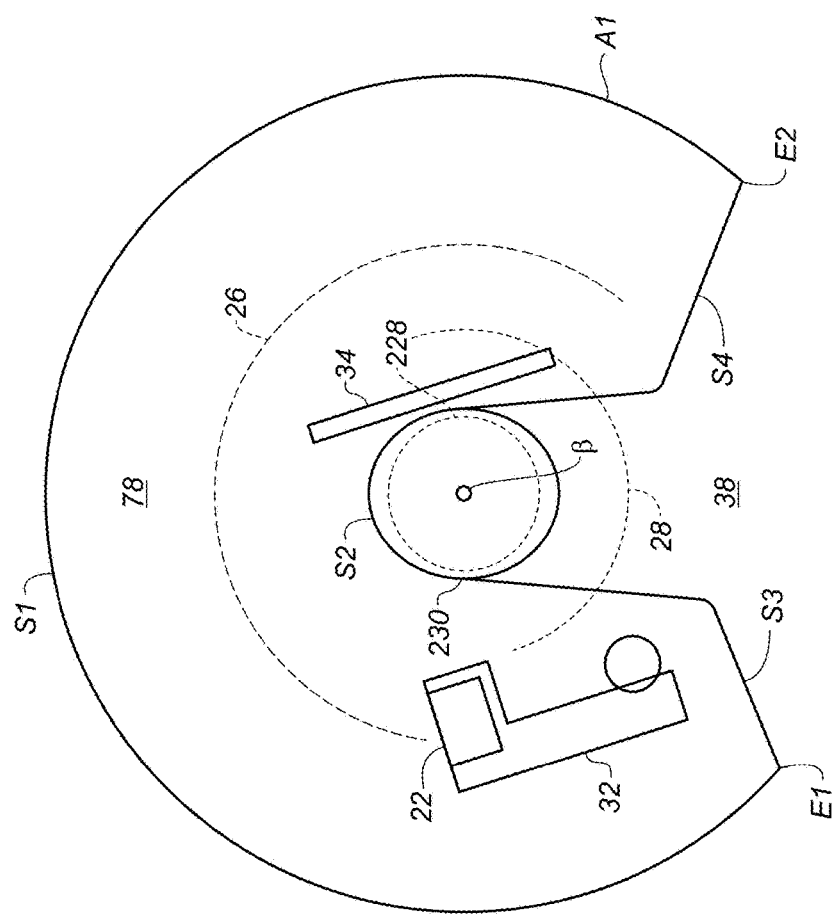
FIG. 17A is a top view of the imaging scanner with a number of its internal imaging components shown, at one extreme end of the imaging scan.
Figure 17B:
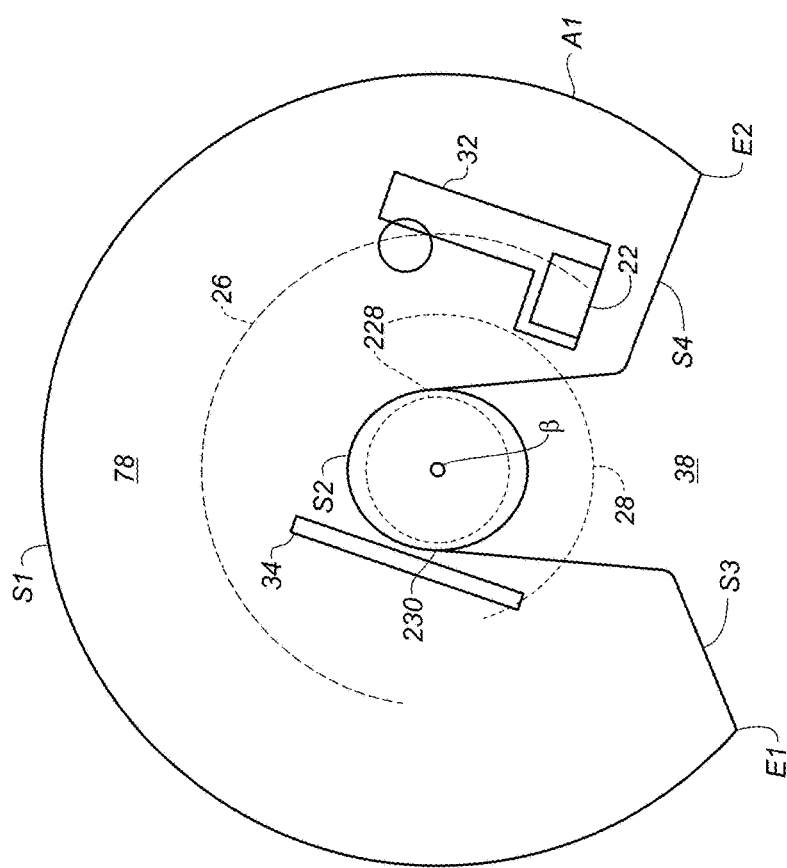
FIG. 17B is a top view of the imaging scanner with a number of its internal imaging components shown, at the opposite extreme end of the imaging scan from that shown in FIG. 17A.
Figure 17C:
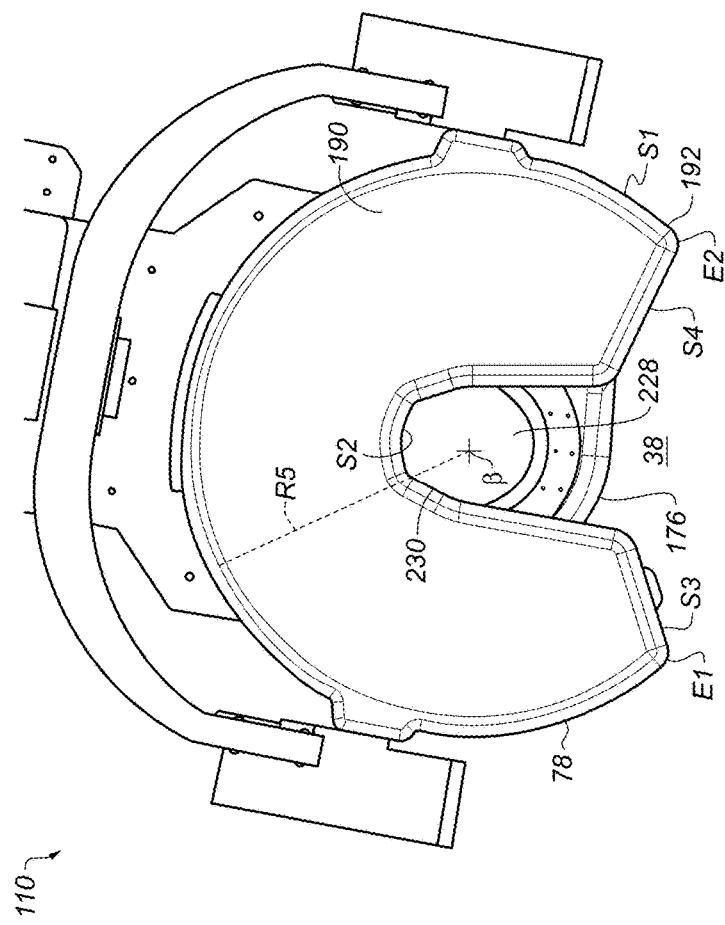
FIG. 17C is a top view of the imaging scanner with its housing shown.

FIGS. 17A-17D show a number of features that are of interest for an understanding of how scanner 110 is configured and operated (e.g., scans). FIG. 17A shows how peripheral gap 38 is formed by housing 78, according to an embodiment of the application. Scan volume 228, outlined with a dashed line, is defined by the source and detector paths 26 and 28, as described previously, and typically includes at least a portion of the β axis. An inner central volume 230 can be defined by surface S2 of housing 78 and can typically enclose scan volume 228. Inner central volume 230 can also be defined by door 176 when closed, as shown in FIG. 17C. Peripheral gap 38 is contiguous with inner central volume 230 when door 176 is in open position (e.g., fully or partially opened).

FIG. 17A shows source transport 32 and detector transport 34 at one extreme end of the scan path, which may be at either the beginning or the end of the scan. FIG. 17B shows source transport 32 and detector transport 34 at the other extreme end of the scan path. It should be noted that source 22 is offset along source transport 32. With this asymmetry, the extent of travel of source 22 relative to surface S3 of housing 78 differs from its extent of travel relative to surface S4. At the extreme travel position shown in FIG. 17B, source 22 is more than twice the distance from surface S4 as source 22 is from surface S3 at the other extreme travel position shown in FIG. 17A. In one embodiment, the inventors use this difference to gain additional clearance for patient positioning with the patient seated.

FIG. 17C shows the configuration of housing 78. In the context of the present disclosure, top surface 190 is considered to be aligned with the top of, at least partially above, or above scan volume 228; bottom surface 192 is aligned with the bottom of, at least partially below, or below scan volume 228. In one embodiment, the top surface 190 or the bottom surface 192 can intersect a portion of the scan volume 228. As shown in FIG. 17C, scan volume 228 can be cylindrical or circularly cylindrical. However, exemplary embodiments of the application are intended to be used with other known 2D scan areas and/or 3D scan volumes. The cover of housing 78 can be metal, fiberglass, plastic, or other suitable material. According to an embodiment, at least portions of top and bottom surfaces 190 and 192 are substantially flat.

Figure 17D:
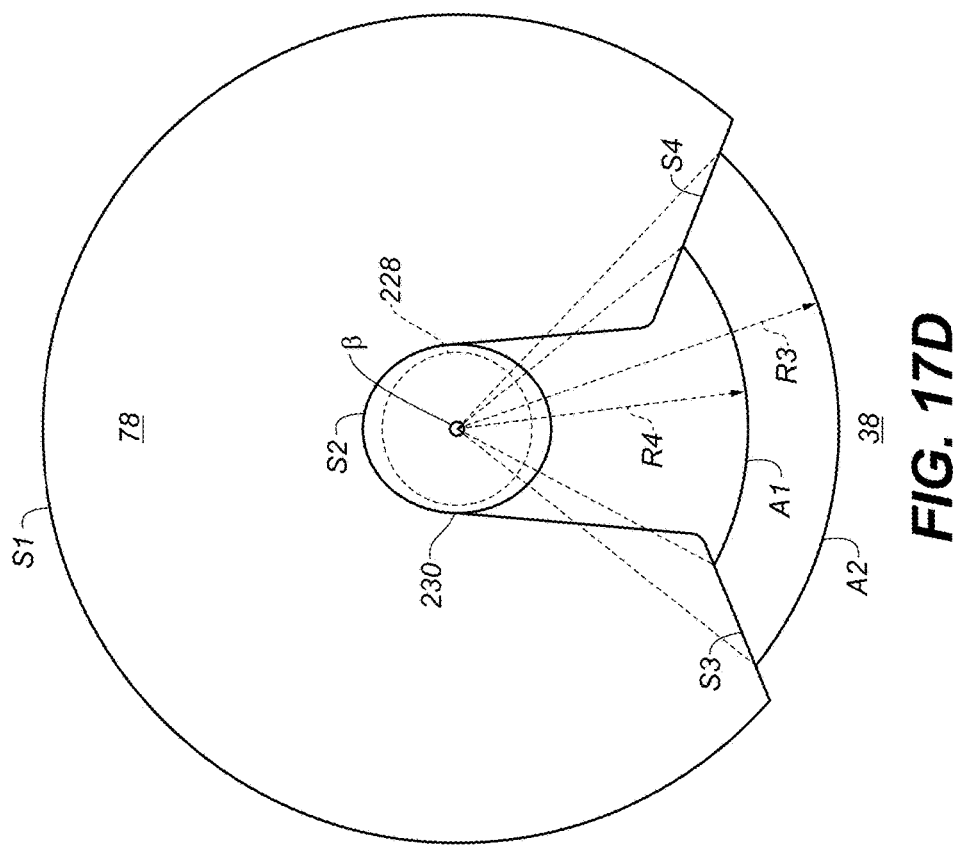
FIG. 17D is a top view of the imaging scanner with internal imaging components and central arc angles shown.

As shown in FIGS. 17A-17C, the scanner 110 has a number of surfaces that define its shape and the shape of peripheral gap or opening 38:

(i) an outer connecting surface S1 extends between a portion of top surface 190 and a portion of bottom surface 192 to at least partially encompass the source and detector; at least a portion of the outer connecting surface extends outside the path the source travels while scanning; embodiments of the outer connecting surface S1 shown in FIGS. 17A-17C provide an arcuate surface that is generally circular at a radius R5 about center β and that extends, between edges E1 and E2 of the housing;

(ii) an inner connecting surface S2 extends between a portion of the first surface and a portion of the second surface to define an inner central volume 230 that includes a portion of scan volume 228; in the embodiment shown in FIG. 17D, inner connecting surface S2 is approximately at a radius R4 from the β axis. At least portions of inner connecting surface S2 can be cylindrical.

(iii) other connecting surfaces can optionally include a surface S3 that corresponds to a first endpoint of the travel path for source transport 32 (FIGS. 17A-17B) and is adjacent to curved surface S1 along an edge E1, wherein surface S3 extends inward toward curved inner surface S2; and a surface S4 that corresponds to a second endpoint at the extreme opposite end of the travel path from the first endpoint for source transport 32 and is adjacent to curved surface S1 along an edge E2 wherein surface S4 extends inward toward curved inner surface S2. According to an embodiment, surfaces S3 and S4 are substantially flat and the angle between surfaces S3 and S4 is greater than about 90 degrees. In general, other additional surface segments (e.g., short linear or curved surface segments) may extend between or comprise any of surfaces S1-S4.

Inner and outer connecting surfaces S1, S2, and, optionally, other surfaces, define peripheral gap or opening 38 that is contiguous with the inner central volume 230 and extends outward to intersect the outer connecting surface S1 to form gap 38 as an angular recess extending from beyond or toward where the outer connecting surface S1 would, if extended, cross the opening 38. As shown in FIG. 17D, a central angle of a first arc A1 that is defined with a center located within the scan volume and between edges of the peripheral gap 38 determined at a first radial distance R4 outside the scan volume is less than a central angle of a second arc A2 that is defined with the first arc center and between the edges of the peripheral gap 38 at a second radial distance R3 outside the scan volume, where the second radial distance R3 is greater than the first radial distance R4. In one embodiment, as shown in FIG. 17D, a first distance that is defined between edges of the peripheral gap 38 determined at a first radial distance R4 outside the scan volume is less than a second distance between the edges of the peripheral gap 38 at a second radial distance R3 outside the scan volume, where the second radial distance R3 is greater than the first radial distance R4. According to one embodiment, arcs A1 and A2 are centered about the β axis, as shown in FIG. 17D and edges of gap 38 are defined, in part, by surfaces S3 and S4 of housing 78.

The needed room for patient anatomy, such as that described with reference to FIG. 10, can be provided when the central angle for arc A2 is large enough to accommodate the extremity that is to be imaged. According to one embodiment, the central angle for arc A2 between edges of gap 38 exceeds the central angle for arc A1 by at least about 5 degrees; more advantageously, the central angle for arc A2 exceeds the central angle for arc A1 by at least about 10 or 15 degrees.

The perspective views of FIGS. 8-14 showed various configurations of extremity CBCT imaging apparatus 100 for imaging limbs of a patient. For each of these configurations, the limb or other extremity of the patient must be positioned at the center of scanner 110 and space must be provided for the paired extremity. As described herein, peripheral gap or opening 38 is provided to allow access space for the patient and room for other parts of the patient anatomy. Door 176 is withdrawn into the housing 78 until the patient is positioned; then, door 176 is pivoted into place in order to provide a suitable transport path for the imaging receiver, detector 24, isolated from the patient being imaged.

FIG. 16A shows scanner 110 with door 176 in open position, not obstructing opening 38, that is, keeping opening 38 clear, allowing patient access for extremity placement within opening 38. FIG. 16C is a top view that shows scanner 110 with door 176 in closed position, held by a latch 92. Door 176 thus extends into the opening 38, enclosing a portion of opening 38 for imaging of the patient's extremity. A sensor 82 provides an interlock signal that indicates at least whether door 176 is in closed position or in some other position. Movement of internal scanner 110 components such as c-shaped gantry 36 is prevented unless the door 176 is latched shut. A release 90 unlatches door 176 from its latched position. As shown in FIGS. 16C and 16D, handle 76 can be positioned outside of opening 38, such as along surface S1 as shown, for opening or closing door 176. Applicants believe that placement of handle 76 (or other type of door closure device) outside of opening 38 is advantageous for patient comfort when closing or opening door 176. As shown in the exemplary embodiment of FIGS. 16C and 16D, handle 76 is operatively coupled with door 176 so that movement of handle 76 in a prescribed direction, such as along the circumference of scanner 110 housing 78 (e.g., a corresponding direction, or in the clockwise direction shown), causes corresponding movement of door 176 (e.g., in the same direction). In one embodiment, clockwise movement of handle 76 causes clockwise movement of door 176, extends door 176 into the opening, and closes door 176; counterclockwise movement of handle 76 causes counterclockwise movement of door 176 and opens door 176, so that it does not obstruct the opening or moves to a position that is clear of the opening.

According to one embodiment, the door 176 is manually pivoted, closed, and opened by the operator. This allows the operator to more carefully support the patient and the extremity that is to be imaged. According to an alternate embodiment, an actuator is provided to close or open the door automatically.

Figure 18:
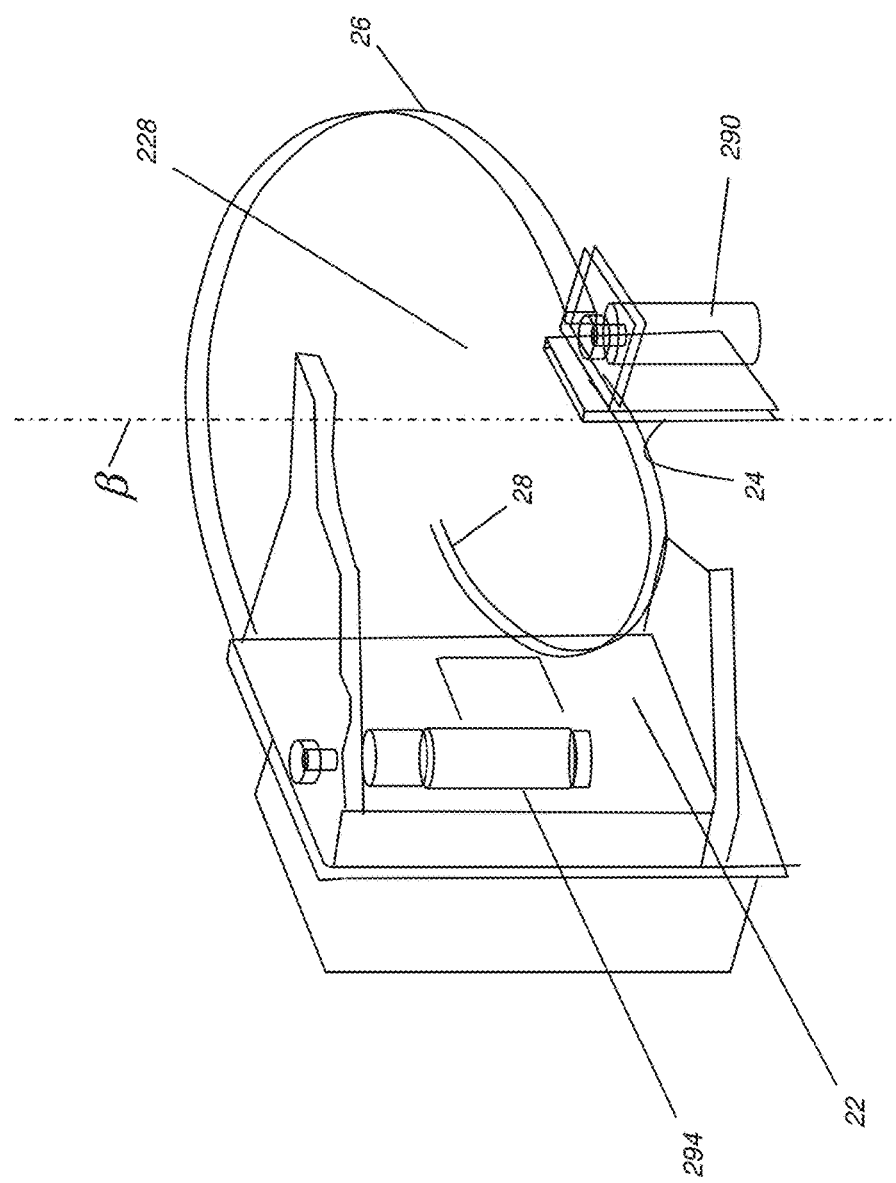
FIG. 18 shows partial paths of scanner components within the housing for separate actuation of the source and detector for orbit about the scan volume.
Figure 19B:
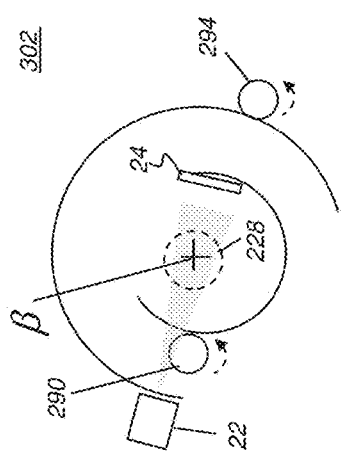
FIGS. 19A-19D are a top view showing the scanning sequence when using two separate actuators for detector and radiation source.
Figure 19D:
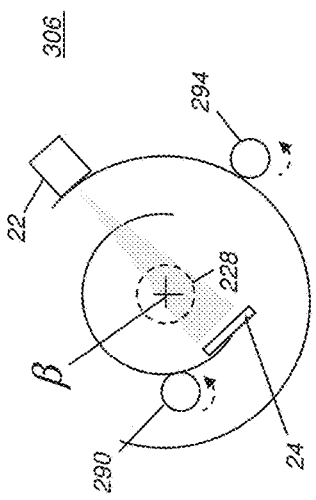
Figure 19A:
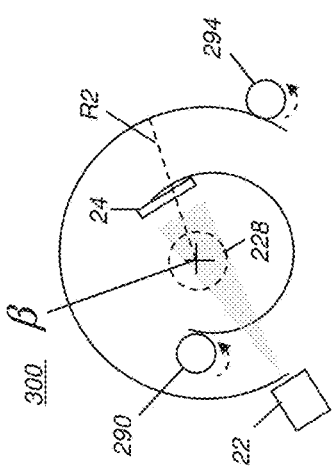
Figure 19C:
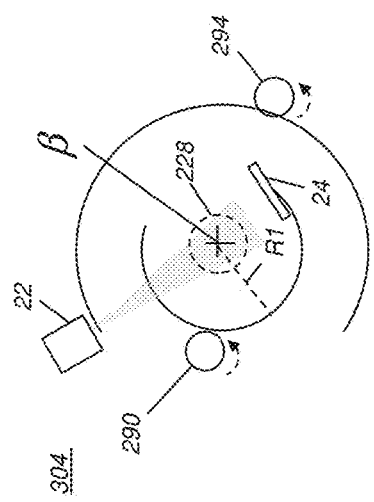

FIG. 18 shows partial paths of scanner components within housing 78 for separate actuation of the source 22 and detector 24 for orbit about the scan volume 228 that is centered about the β axis. A radiation source actuator 294 translates radiation source 22 along source path 26. Independent of the radiation source 22 movement, a detector actuator 290 translates detector 24 along detector path 28. The combined and coordinated movements of radiation source actuator 294 and detector actuator 290 cooperate to provide the scan action needed for acquiring the volume image data from scan volume 228.

FIGS. 19A-19D show a schematic top view of the scanning components of FIG. 18 as they orbit the scan volume 228 about the β axis. Scanning begins with components at position 300 and progresses to position 302, position 304, and position 306. In the example shown, coordinated rotation of actuators 290 and 294 causes orbital movement of source 22 and detector 24 about scan volume 228. Source 22 orbits along a radius R2. Detector 24 orbits along a shorter radius R1.

Separate actuation for the source 22 and detector 24 components allows one or the other to be separately moved, which can be convenient for patient positioning or for storage or transport of the imaging apparatus.

Radiation-absorbent shielding is provided within housing 78 and about the enclosed components in order to help absorb stray and scattered radiation. As shown in FIG. 20

(with top surface 190 removed for visibility of internal components), shielding 250 is added to either or both the inner or outer surfaces of housing 78, including top and bottom surfaces 190, 192 as well as side surfaces that extend between top and bottom surfaces. Shielding 250 is typically lead or some other radiation-absorbent material and may be provided in sheet form, fitted against and coupled to housing 78. In gantry 36, detector 24 is coupled to a shielded back plate 252 to absorb radiation that might pass through and around detector 24. Shielding 250 can also be provided on surfaces of door 176, including along closure portion 188.

In the perspective view of gantry 36 given in FIG. 21, it can be seen that shielding 250 is also provided along straight and curved surfaces that extend between source 22 and detector 24. In addition, a backing plate 252 provides a shielding function, blocking x-rays from source 22. In position behind detector 24, backing plate 252 also serves as a counterweight to help balance gantry 36 as it rotates through its scan cycle. The use of backing plate 252 as counterweight helps to move the center of gravity of gantry 36 toward its center of rotation. In one embodiment, the backing plate can move a center of gravity of the scanner 110 (e.g., source, C-ring, detector) to the beta axis.

It should be noted that, in order to provide a clear path between source 22 and detector 24 at all positions of these components during exposure, shielding cannot be provided on surfaces of housing that surround and define opening 38. Thus, some additional radiation-absorbent shielding for the patient and technician may be helpful for some exam types.

Certain exemplary system and/or method embodiments according to the application can provide a tomosynthesis imaging capability. In one embodiment, the scanner 110 can also support tomosynthesis, which can provide an image with less rotation than a CT scan. Generally, the source 22 and the detector 24 travel about 40 degree path while aiming the scan volume. However, embodiments according to the application can provide a tomosynthesis imaging capability over a range of 30-80 degrees relative to a scan volume or patient extremity. In one embodiment, the scanner 110 or system 100 provide the tomosynthesis imaging capability or mode in addition to the CBCT imaging capability or mode.

Figure 22:
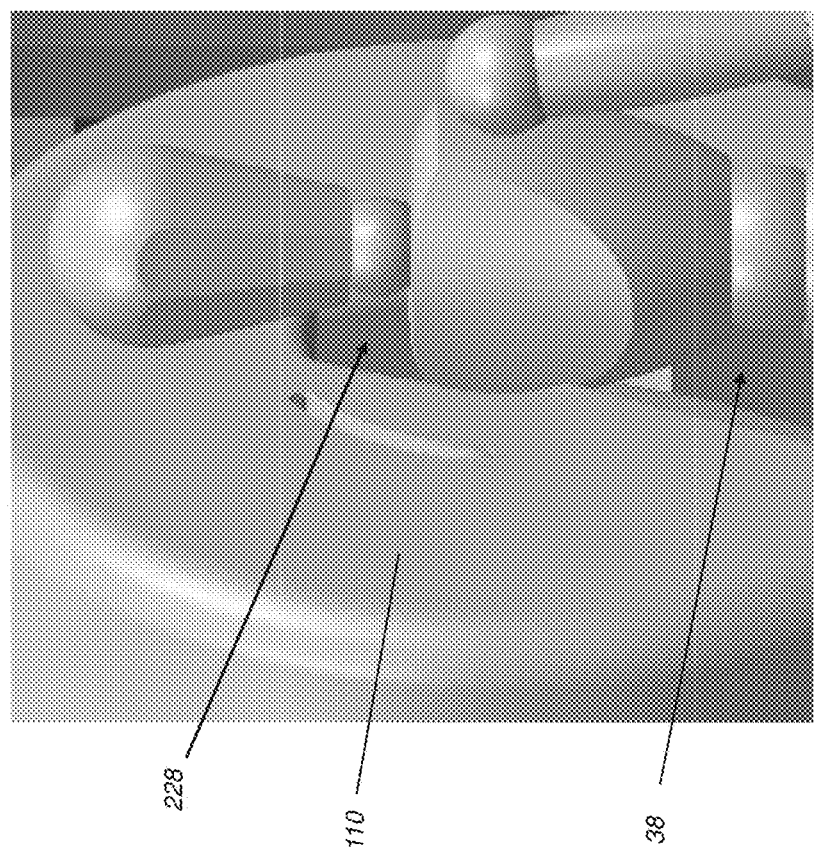
FIG. 22 is a diagram that shows another exemplary embodiment for tomosynthesis imaging conducted by a CBCT imaging apparatus according to embodiments of the application.

FIG. 22 is a diagram that shows an exemplary embodiment for tomosynthesis imaging conducted by a CBCT imaging apparatus. As shown in FIG. 22, a shoulder of a patient is placed in the scan volume 228 of the scanner 110. In FIG. 22, the patient's body is radially aligned with the peripheral gap 38. In one embodiment, the peripheral gap 38 is one feature of the scanner 110 that allows the tomosynthesis imaging capability to be implemented.

Figure 23:
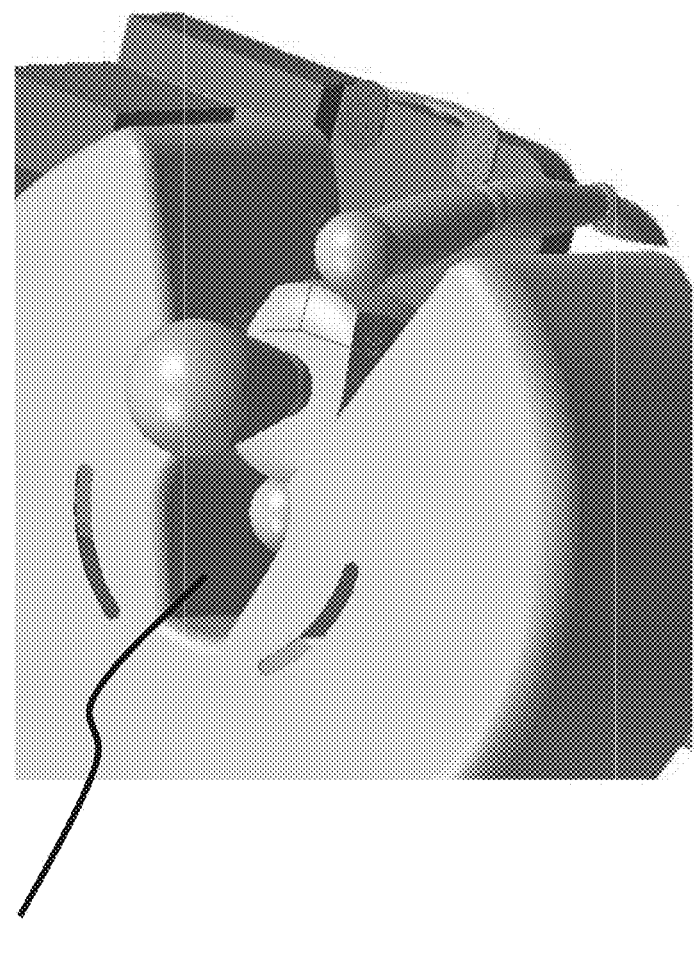
FIG. 23 is a diagram that shows another exemplary embodiment for tomosynthesis imaging conducted by a CBCT imaging apparatus according to embodiments of the application.

FIG. 23 is a diagram that shows another exemplary embodiment for tomosynthesis imaging conducted by a CBCT imaging apparatus. As shown in FIG. 23, a shoulder of a patient is placed in the scan volume 228 of the scanner 110 and the patient's body is aligned parallel to a longitudinal axis of the scan volume 228 (e.g. the β axis) again in the peripheral gap 38. In one embodiment, the apparatus 100 can be configured to provide at least one of coronal tomography imaging, transverse tomography imaging and sagittal tomography imaging.

In one embodiment, the door 176 of the scanner 110 can cover a detector path through the peripheral gap 38. The door 176 can be in an open position in the tomosynthesis imaging mode. In an alternative embodiment, the scanner 110 can include a removable door, to cover the detector path that is removed in the tomosynthesis imaging mode.

In one embodiment, the tomosynthesis imaging conducted by a CBCT imaging apparatus can use independent source and detector actuators. For example, the independent source actuator 294 (FIG. 18) and detector actuator 290 can translate the source 22 and detector 24 using less space in the scanner 110, which can allow for additional movement in the scanner 110 or a larger peripheral gap. In another embodiment of the tomosynthesis imaging provided by the CBCT imaging apparatus 100, a subset of CBCT projection data can be collected during an imaging scan (or selected from the entire set of CBCT projection data) and used to generated 3D tomography images to reduce metal artifacts.

As described previously, tomosynthesis employs a limited angle reconstruction and acquires and processes a small subset of the total number of projections typically used for CBCT.

Applicants have developed a system and solution that employs cone beam computed tomography (CBCT) acquisition data for optional tomosynthesis rendering. The Applicants' approach uses the x-ray projection data from the CBCT acquisition to generate alternative types of reconstructions, more specifically tomosynthesis views.

Applicants have recognized the need for metal artifact visibility in medical images. At least one benefit of the Applicants' system and method relates to the context of orthopedic imaging in that it is intended to provide reconstructions with improved boundary visibility between metal implants and/or other hardware such as screws and the surrounding bone/tissue. Clinical situations where this is helpful include implant loosening, improperly placed screws, screw loosening, bone/implant fusion assessment, and the like. Other benefits of such a method may include reduction of other image artifacts in plane.

Another benefit of the Applicants' solution is an "on-demand" tomosynthesis reconstructions of CBCT data in a viewer/display so as to reduce or eliminate metal artifacts. A further benefit of the Applicants' approach is that, with a given CBCT acquisition, no additional, separate tomosynthesis data acquisition is needed, allowing multiple representations for acquired projection image data.

Other benefits may become apparent, for example, noise reduction or adaptation to viewer preference.

Methods and apparatus for scatter correction for CBCT systems and cone beam imaging reconstruction are described, for example, in U.S. Pat. No. 8,818,065 granted on Aug. 26, 2014 titled "METHODS AND APPARATUS FOR SCATTER CORRECTION FOR CBCT SYSTEM AND CONE-BEAM IMAGE RECONSTRUCTION", the entirety of which is incorporated herein by reference.

Figure 24:
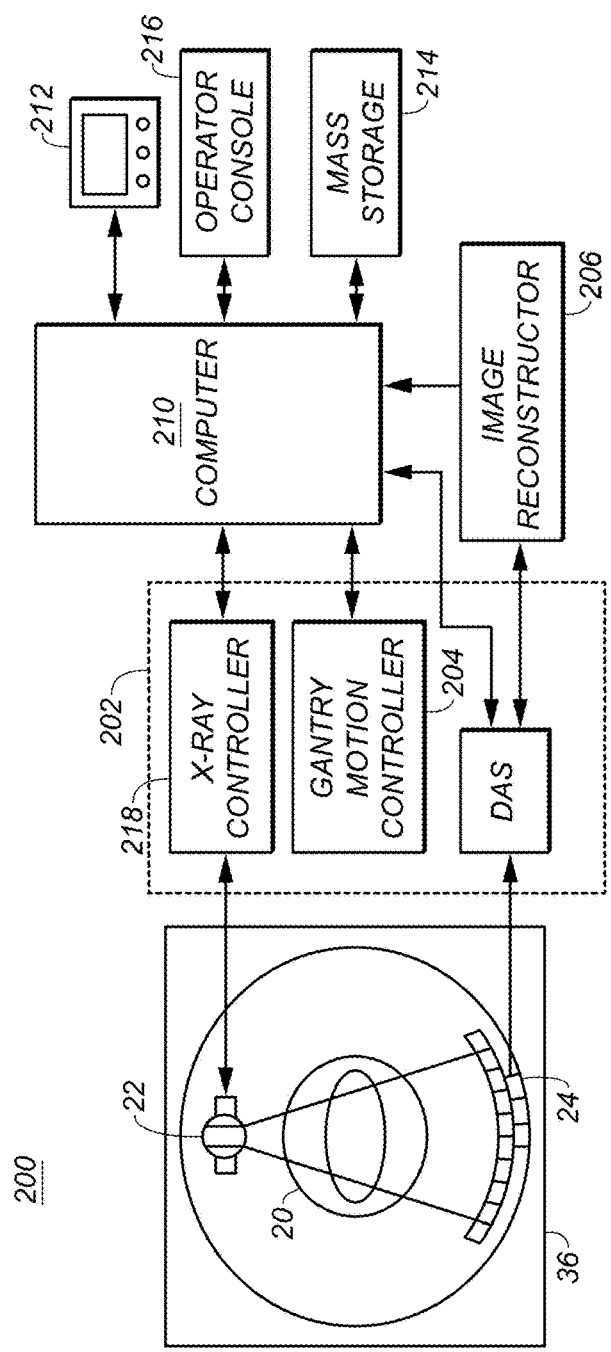
FIG. 24 shows a schematic block diagram of a generalized image acquisition system that forms a part of a conventional CBCT or CT imaging system.

With reference to FIG. 24, there is shown a block diagram of a generalized image acquisition system 200 that forms a part of a conventional CBCT or CT imaging system. Such a system includes gantry 36 supporting an x-ray source 22 that projects a beam or cone beam of x-rays toward a digital detector (detector array) 24 on the opposite side of gantry 36. The detector 24 is formed by a plurality of detector elements which together sense the projected x-rays that pass through a patient or other subject 20. Each detector element produces an electrical signal that represents the intensity of an impinging x-ray beam and its attenuation.

During the scan to acquire x-ray projection data, the gantry 36 and, accordingly, the components mounted thereon, rotate about a center of rotation located within subject 20. The rotation of the gantry and the operation of the x-ray source are controlled by a controller 202 or other suitable control mechanism of the system. The controller 202 provides power and timing signals to the x-ray source 22 and a gantry motor controller 204 that controls the rotation and rotation speed/position of the gantry. A Data Acquisition System (DAS) samples data from the detector elements and converts the data to digital signals for subsequent processing. An image reconstructor 206 receives sampled and digitized x-ray data from DAS and performs (high speed) image reconstruction. The reconstructed image is applied as an input to a computer 210 which displays the image on a display monitor 212, or transmits and/or stores the image/data to a mass storage device 214. The computer 210 receives commands and scanning parameters from an operator via a console 216 that has at least one entry device (such as a keyboard or mouse). The associated display monitor 212 allows an operator to observe the reconstructed image and/or other data from the computer. The operator supplied commands and parameters are sued by the computer to provide control signals and information to the DAS, an x-ray controller 218, and the gantry motor controller 204.

Figure 25:
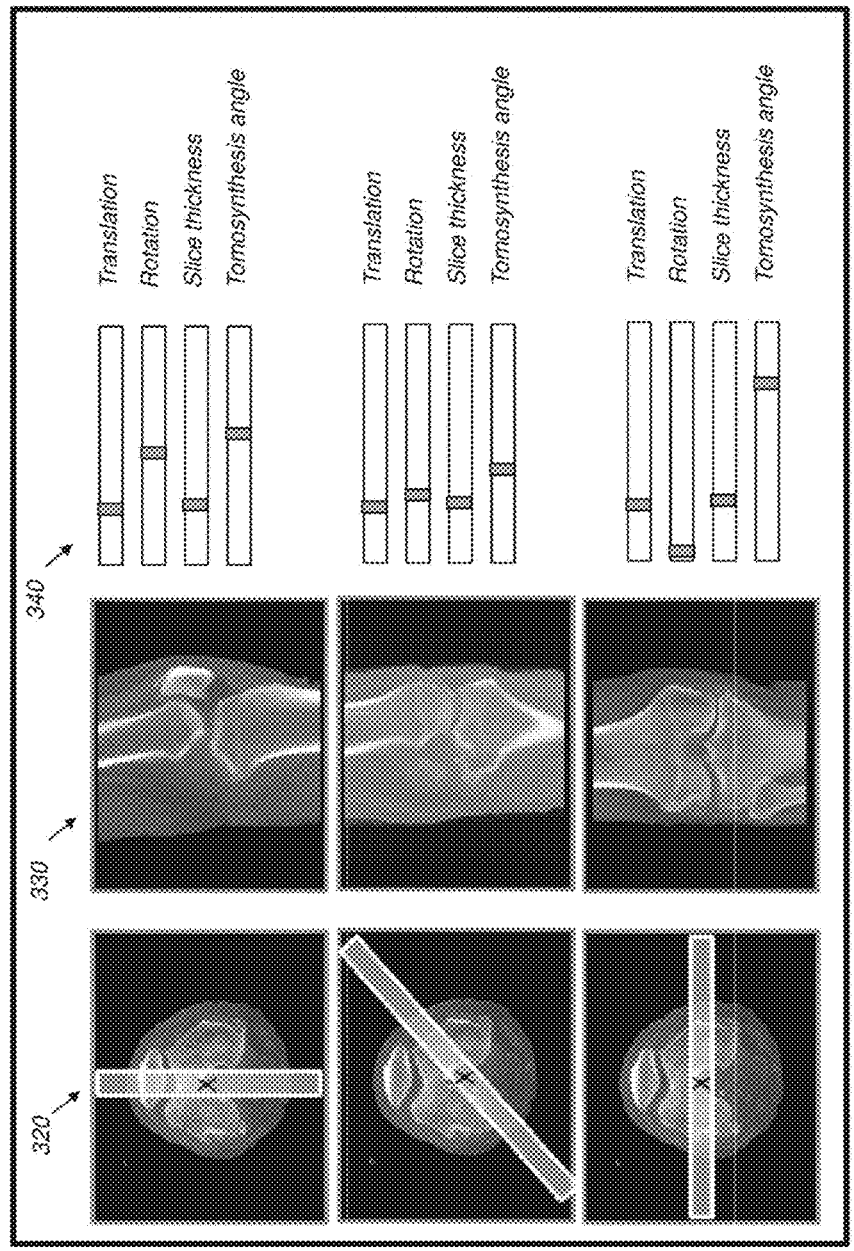
FIG. 25 shows a plurality of images viewable on a display by an operator/radiologist, in accordance with this disclosure.

FIG. 25 shows a plurality of images viewable on a display by an operator/radiologist, in accordance with this disclosure. More particularly, there are shown three rows of images, wherein each row provides corresponding images of an axial slice view and a tomosynthesis view, and provides controls to modify the displayed images, including controls for translation, rotation, displayed slice thickness, and tomographic angle, which selects the displayed angle for the generated image. In the figure, the controls are shown as slider bars, though those skilled in the art will recognize other controls/methods which can be employed for this function. Slice thickness controls the presentation of the tomosynthesis view.

Figure 26B:
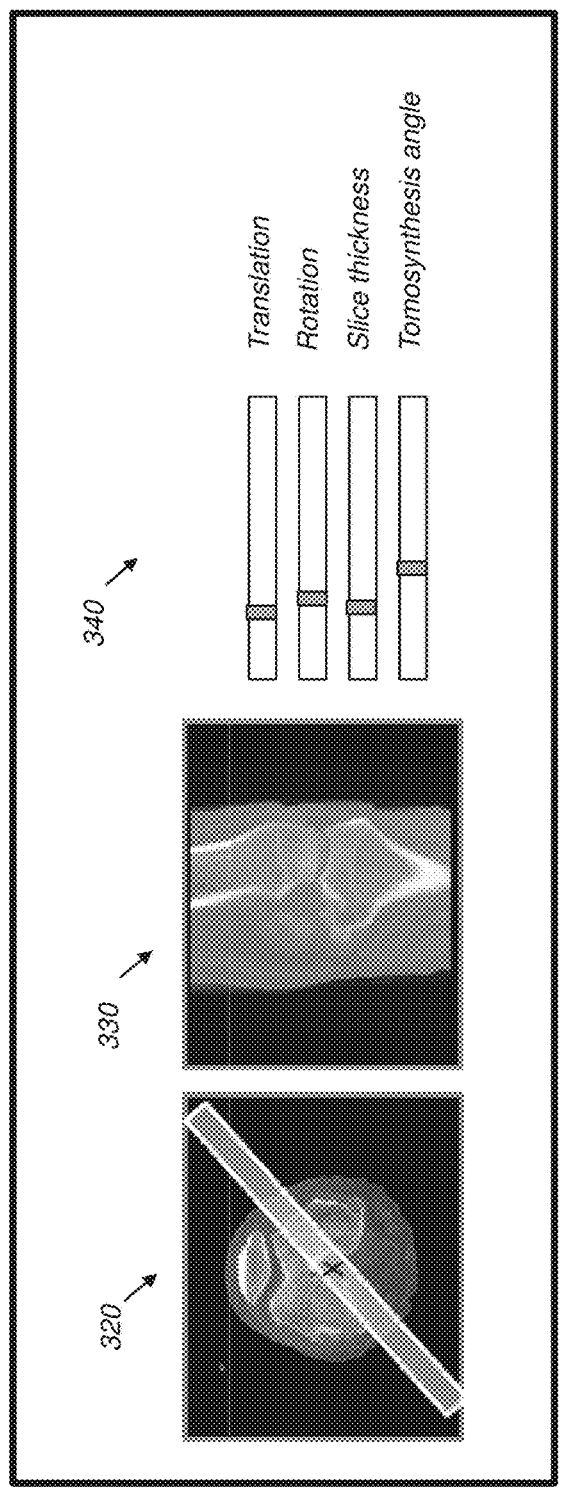

FIGS. 26A and 26B show first and second rows, respectively, of images shown in FIG. 25. As shown, the values of the controls differ between FIG. 26A and FIG. 26B. Accordingly, the displayed axial slice view and tomosynthesis view are different since the rotation control value is different between FIG. 26A and FIG. 26B.

Figure 27:
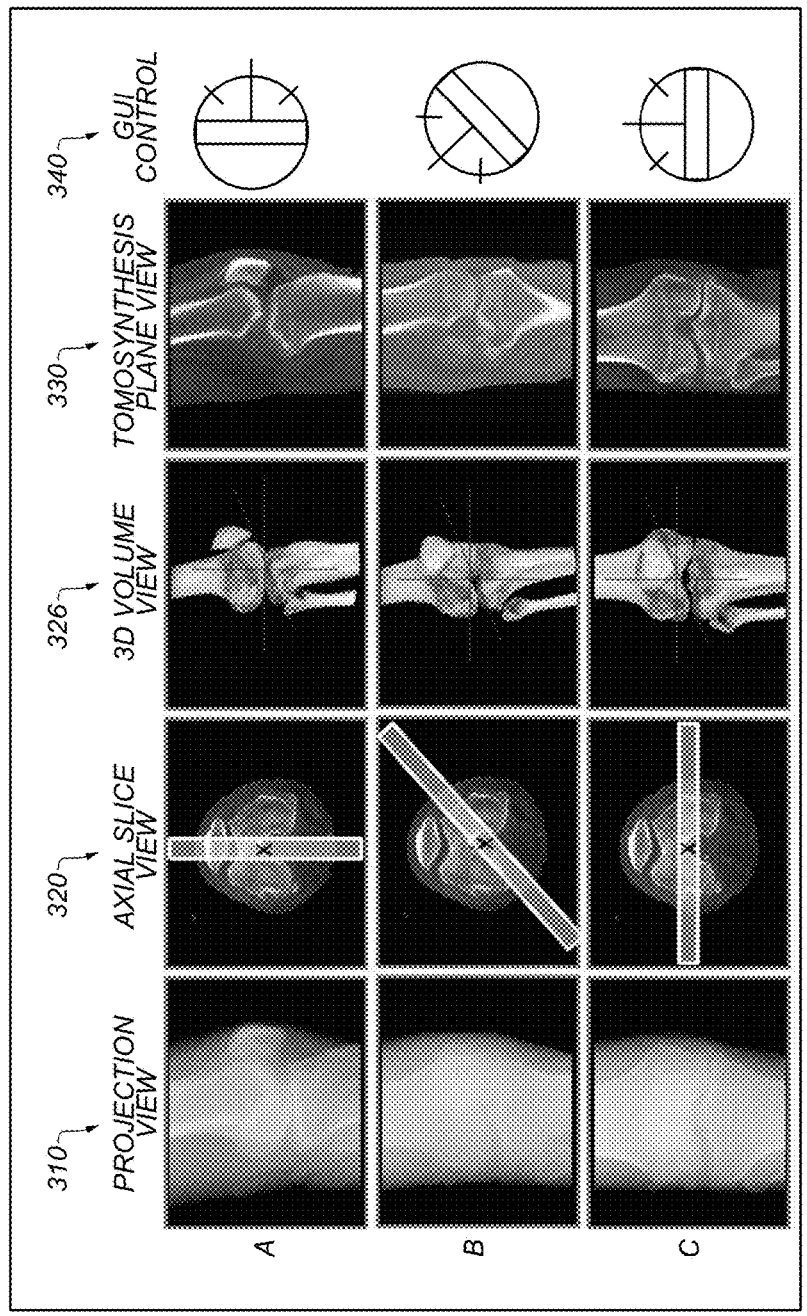
FIG. 27 shows a number of images viewable on a display by an operator or practitioner, in accordance with this disclosure.

FIG. 27 shows a number of images viewable on a display by an operator or practitioner, in accordance with this disclosure. In particular, there are shown multiple synchronized tomosynthesis views 330 to demonstrate how different views could be used to select a tomosynthesis plane. The "x" mark in axial slice views 320 indicate the axis of rotation. Rows A through C show corresponding images of a projection view 310, axial slice view 320, 3D volume view 326, tomosynthesis view 330, and associated GUI (graphic user interface) control 340. The projection view 310 shows a projection image taken at the selected angle.

Figure 28:
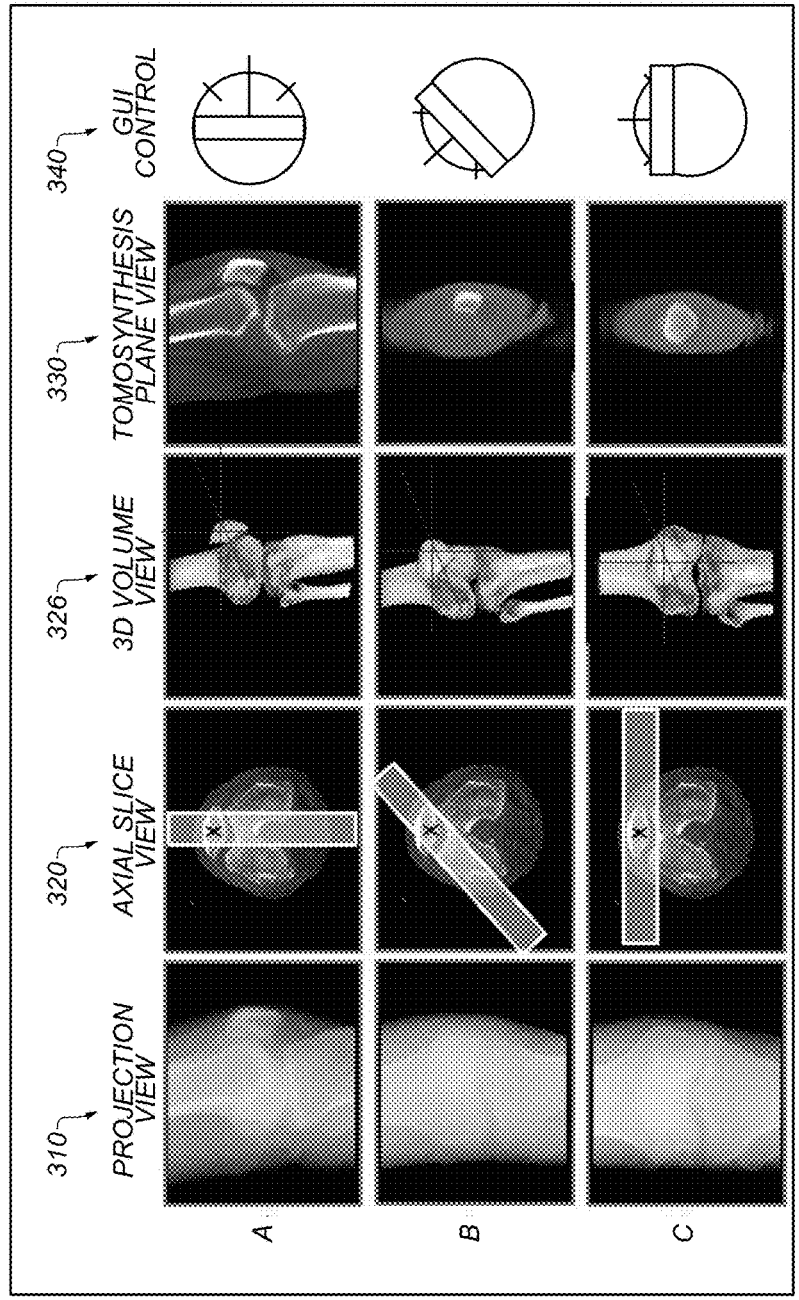
FIG. 28 shows another set of images viewable on a display by an operator or practitioner, in accordance with this disclosure with slice thickness and location differences from the display of FIG. 27.

FIG. 28 shows another set of images viewable on a display by an operator or practitioner, in accordance with this disclosure with slice thickness and location differences from the display of FIG. 27. FIG. 28 shows multiple synchronized tomosynthesis views to demonstrate how different views can be used to select a tomosynthesis plane. The "x" mark indicates the axis of rotation. Rows A through C show corresponding images of a projection view, axial slice view, 3D volume view, tomosynthesis view, and associated GUI (graphic user interface) control.

Figure 29B:
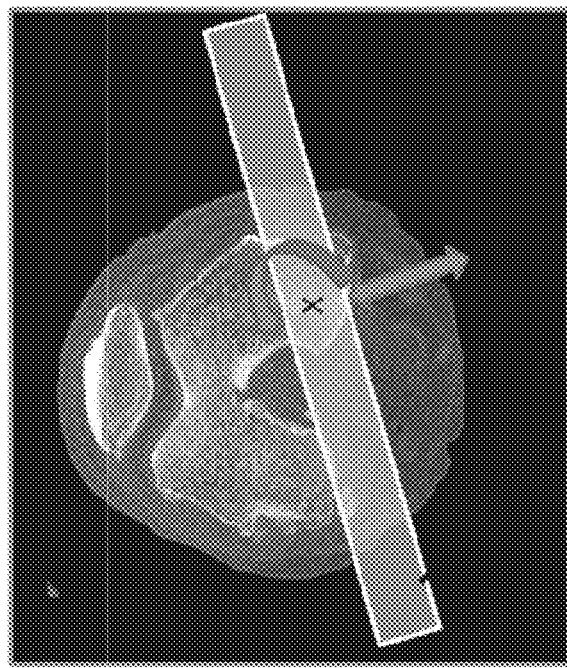
FIGS. 29A and 29B show images viewable on a display by an operator/radiologist, in accordance with this disclosure.
Figure 29A:
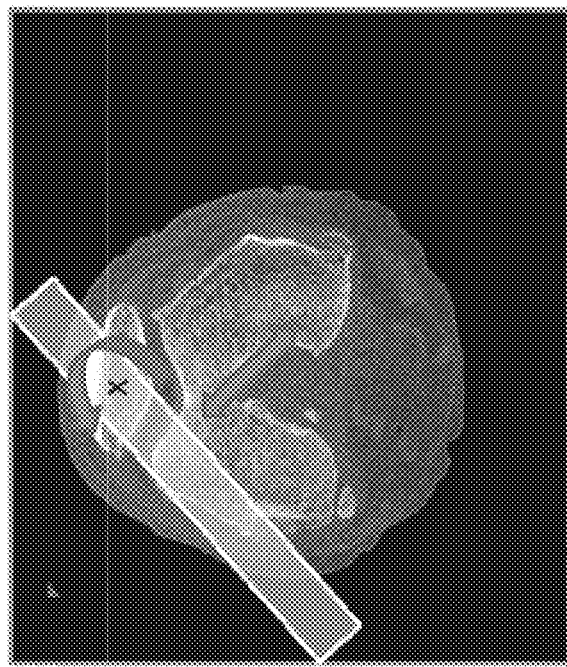

FIGS. 29A and 29B show a set of images of axial slice views 320 viewable on a display by an operator or practitioner, in accordance with this disclosure.

Figure 30:
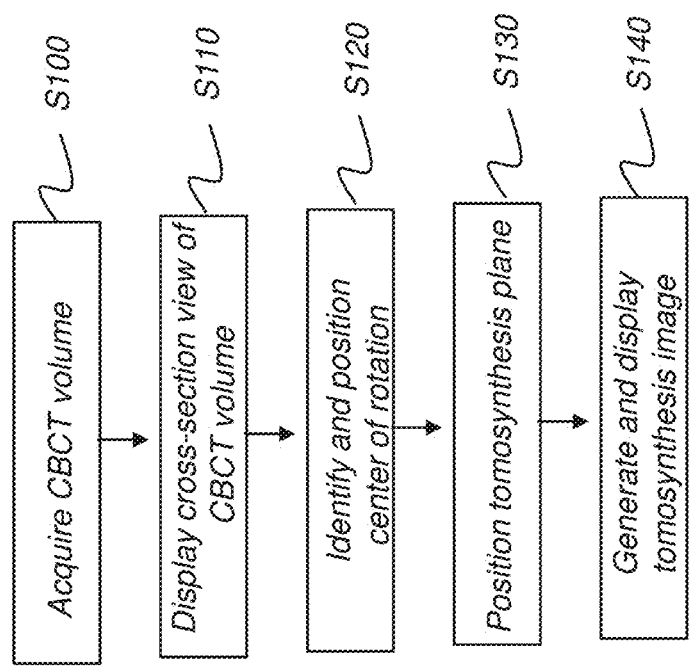
FIG. 30 is a logic flow diagram that shows a sequence for obtaining tomosynthesis views from CBCT volume data according to an embodiment of the present disclosure.

The logic flow diagram of FIG. 30 shows a sequence for obtaining tomosynthesis views from CBCT volume data according to an embodiment of the present disclosure. In an acquisition step S100, the system obtains projection data and a reconstructed CBCT volume image of a subject, such as an arm, leg, knee, or other extremity of a patient. In a cross-section display step S110, the system displays a suitable cross section view of the reconstructed CBCT volume for accepting viewer instructions, such as the axial view shown in FIGS. 29A and 29B. In a center identification step S120, the system accepts a viewer instruction that positions a center of rotation within the displayed cross section view from step S110. In response, the system displays the center of rotation at a central location within the cross section view, such as by displaying the "x" symbol or other suitable markup, as shown in FIGS. 29A and 29B, for example. The viewer can translate the center of rotation to some alternate position within the cross-sectional view. Where the operator console 216 is a touch screen (FIG. 24), the viewer can reposition the "x" symbol on the GUI directly across the screen. Alternately, a mouse pointer or keyboard command could be used for translating the position of the center of rotation. The tomosynthesis reconstruction plane can then be defined and positioned, centered at the center of rotation. A plane positioning step S130 allows rotation of the tomosynthesis plane about the specified center of rotation. To perform this function, a touch screen GUI can allow the viewer to rotate the tomosynthesis reconstruction plane and to view the rotation angle of plane 344 as shown in FIGS. 25-29. In addition, the GUI can also be used to adjust the thickness of the tomosynthesis plane as an optional part of step S130. An image generation step S140 then generates and displays the resulting tomosynthesis image.

An embodiment of the present disclosure is advantaged where metal artifacts are visible in the CBCT reconstruction. The capability for providing an alternative tomosynthesis representation can help to either minimize the effect of the artifact on surrounding portions of the image volume or to more accurately visualize the fastener or other metal object that is in the image content.

With regard to tomosynthesis reconstruction plane selection, a viewer can select a plane of a tomosynthesis reconstruction from the GUI using one or more views of cone beam CT data. For example, the user can do one or more of the following:
 (i) Select the plane from a 3D volume or surface rendering.
 (ii) Select the plane from a view of orthogonal slice planes (e.g. axial, transverse, and/or oblique) as described hereinabove.
 (iii) Select the plane from a view of the 2D projections.
 (iv) Select the plane from a graphical control placed on the GUI.

With regard to rotation axis selection, a viewer can select a rotation axis of the tomosynthesis viewing planes, as described above. The planes can be centered on or around any suitable axis as designated by the viewer, as opposed to rotating about the rotation axis or center of the volume.

With regard to selectable parameters, the operator can specify viewing variables such as slice thickness, the desired direction of the reconstruction plane, the angular range around the selected direction, and the rotation axis of the tomosynthesis plane.

With regard to selection of oblique planes, tomosynthesis planes at oblique angles can be generated from a plurality of x-ray sources. Planes can be positioned along or near to the rotation axis, with independent planes for each source and with combined data from sources to generate intermediate planes.

With regard to selection of full 360 degrees with partial scan data, when the cone beam data is taken at less than 360 degrees, the full range of planes over 360 degrees can still be viewed.

With regard to selection of reconstruction plane direction from projection data, a slide bar or other control mechanism can be used to control the displayed projection data to select the tomosynthesis reconstruction plane. The tomosynthesis reconstruction plane can be superimposed on the same window or shown in a separate window.

With regard to synchronization of multiple views, multiple presentations of the data can be synchronized to provide complementary views of the same tomosynthesis reconstruction plane. In this way, when the current tomosynthesis plane changes in one view, other views update to reflect that change. This allows:

(i) Indicating or changing the tomosynthesis plane in the tomosynthesis window (rotation angle or slice position).

(ii) Indicating or changing the tomosynthesis plane on a 3D rendered view.

(iii) Indicating or changing the tomosynthesis plane from the projection data.

(iv) Indicating or changing the tomosynthesis plane from changing the current slice of an axial or transverse view of the reconstruction data, including a general multiplanar reconstruction (MPR) plane.

With regard to interactive reconstruction tomosynthesis reconstruction is preferably accomplished interactively, on demand. Options include:

(i) Reconstruction done using an iterative reconstruction technique.

(ii) Reconstruction done using an analytical reconstruction technique (iii) Preprocessing of the projection data is done in advance to speed up reconstruction time, such as prefiltering images for analytical reconstruction or prefiltering images for analytical reconstruction at different slice thicknesses, where interpolation could be used to generate intermediate filter levels.

With regard to metal artifact reduction, tomosynthesis reconstruction includes algorithms for reconstructing metal or high contrast objects to improve the interface with soft tissue and allows use of metal artifact reduction techniques.

With regard to selection of high contrast objects, the viewing interface can be tailored for selecting metal or high contrast objects for inspection, wherein an algorithm identifies the high contrast object and configures the display for inspection of the object.

With regard to task specific reconstruction protocols, there can be reconstruction parameter protocols for specific clinical tasks.

Applicants have described an imaging method, comprising: accessing a cone beam computed tomography (CBCT) data; displaying, on a display, at least one view of the CBCT data; providing an interface for a user to indicate a plane on the displayed at least one view of the CBCT data; and displaying a tomosynthesis image on the display in response to an indication of a plane from the user.

Applicants have described a method where the user guides/selects/indicates a plane of tomosynthesis reconstruction from viewing reconstructed cone beam CT data. The plane can be selected from a 3D surface rendering, from orthogonal slice planes (e.g.: axial, transverse, or oblique), and/or from 2D projections.

What we claim is:

1. An imaging method, comprising:
   accessing cone beam computed tomography (CBCT) data;
   displaying, on a display monitor, at least one view of the CBCT data;
   providing an interface for a user to indicate a tomosynthesis reconstruction plane on the displayed at least one view of the CBCT data;
   using the CBCT data, generating a tomosynthesis image according to the tomosynthesis reconstruction plane indicated using the interface; and
   displaying the generated tomosynthesis image on the display monitor.

2. The imaging method of claim 1, further comprising simultaneously displaying the CBCT data and the tomosynthesis image on the display monitor.

3. The imaging method of claim 1 wherein displaying the at least one view of the CBCT data comprises displaying an axial view of the CBCT data.

4. The imaging method of claim 3 further comprising displaying a volume view of the CBCT data.

5. The imaging method of claim 1 further comprising an interface which allows re-positioning of a center of rotation for the tomosynthesis reconstruction plane.

6. The imaging method of claim 1 further comprising providing an interface which allows adjusting of slice thickness for the tomosynthesis reconstruction plane.

7. The imaging method of claim 1 further comprising providing an interface which allows adjusting of the angle of tomosynthesis display.

8. The imaging method of claim 1 further comprising displaying a projection image corresponding to the indicated tomosynthesis reconstruction plane.

9. A method, comprising:
   using an interface displayed on a display, selecting a plane of tomosynthesis reconstruction of a subject from reconstructed cone beam computed tomography (CBCT) data;
   using the CBCT data, generating a tomosynthesis image according to the selected plane of tomosynthesis reconstruction; and
   displaying, storing, or transmitting the generated tomosynthesis image.

10. The method of claim 9 wherein selecting the plane is accomplished by selecting according to a 3D surface rendering.

11. The method of claim 9 wherein selecting the plane is accomplished by selecting from an orthogonal slice or from an oblique slice.

12. The method of claim 9 wherein selecting the plane is accomplished by selecting from 2D projections used to generate the cone beam computed tomography data.

13. The method of claim 9 further comprising:
   using the interface, selecting a rotation axis of a tomosynthesis viewing plane.

14. The method of claim 9 further comprising:
   using the interface, selecting a slice thickness, a desired direction of a reconstruction plane, or an angular range around the selected direction.

15. The method of claim 9 further comprising generating tomosynthesis planes at oblique angles from images acquired using a plurality of x-ray sources.

16. The method of claim 9 further comprising providing a viewing interface for instructing the displayed projection data to select the tomosynthesis reconstruction plane.

17. The method of claim 9 further comprising synchronizing a plurality of presentations to provide a complementary view of the same tomosynthesis reconstruction plane.

18. The method of claim 9 further comprising providing a viewing interface for selecting metal or high contrast objects for inspection.

19. The method of claim 9 further comprising identifying a high contrast object and configuring a viewing interface to inspect the high contrast object.

20. An imaging method, comprising:
acquiring CBCT volume data of a subject;
displaying, on a display, a cross-sectional rendering of the CBCT volume;
in response to a viewer instruction:
   (i) positioning a center of rotation for a tomosynthesis plane on the displayed image; and
   (ii) specifying a rotation angle of the tomosynthesis plane relative to the displayed image;
using the CBCT volume data, generating a tomosynthesis image according to the specified tomosynthesis plane; and
displaying, transmitting, or storing the generated tomosynthesis image.

* * * * *